US011738053B2

(12) United States Patent
Li et al.

(10) Patent No.: US 11,738,053 B2
(45) Date of Patent: Aug. 29, 2023

(54) METHODS AND COMPOSITIONS FOR TREATING CHRONIC GRANULOMATOUS DISEASE

(71) Applicant: THE BOARD OF REGENTS OF THE UNIVERSITY OF TEXAS SYSTEM, Austin, TX (US)

(72) Inventors: Senlin Li, San Antonio, TX (US); Robert A Clark, San Antonio, TX (US); Cang Chen, San Antonio, TX (US); Yang Li, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 500 days.

(21) Appl. No.: 16/329,915

(22) PCT Filed: Sep. 1, 2017

(86) PCT No.: PCT/US2017/049815
§ 371 (c)(1),
(2) Date: Mar. 1, 2019

(87) PCT Pub. No.: WO2018/045266
PCT Pub. Date: Mar. 8, 2018

(65) Prior Publication Data
US 2019/0201449 A1    Jul. 4, 2019

Related U.S. Application Data

(60) Provisional application No. 62/382,872, filed on Sep. 2, 2016.

(51) Int. Cl.
| | |
|---|---|
| *A01N 63/00* | (2020.01) |
| *C12N 15/63* | (2006.01) |
| *C07H 21/04* | (2006.01) |
| *A61K 35/28* | (2015.01) |
| *A61K 38/19* | (2006.01) |
| *A01K 67/027* | (2006.01) |
| *C12N 15/86* | (2006.01) |

(52) U.S. Cl.
CPC .......... *A61K 35/28* (2013.01); *A01K 67/0276* (2013.01); *A61K 38/193* (2013.01); *C12N 15/86* (2013.01); *A01K 2227/105* (2013.01); *A01K 2267/0306* (2013.01); *C12N 2740/16043* (2013.01)

(58) Field of Classification Search
CPC ...... A61K 35/28; A61K 38/193; C12N 15/63; C12N 15/86; C12N 5/0634; C12N 5/0647; C12N 2510/00; C12N 2740/16043; C07H 21/04
See application file for complete search history.

(56) References Cited

U.S. PATENT DOCUMENTS

2006/0018889 A1    1/2006  Li et al.

FOREIGN PATENT DOCUMENTS

| WO | WO 2009/012959 | 1/2009 |
| WO | WO 2015/0171852 | 11/2015 |

OTHER PUBLICATIONS

Dib et al., 2011, J. of Cardiovasc. Trans. Res., 4:177-181.*
Wu et al., 2012, Aging Research reviews, vol. 11, p. 32-40.*
Agrahari et al., 2017, Expert Opinion on Drug Delivery, vol. 14, No. 10, p. 1145-1162.*
Ikonomou et al., 2017, Am J Respir Crit Care Med, vol. 195, p. 13-14.*
Chiriaco et al., 2016, Pediatric Allergy and Immunology, vol. 27, issue 3, p. 242-253, Published on Dec. 17, 2015.*
Ikehara et al., 2013, Frontier in Cell and Developmental Biology, vol. 1, Article 2, p. 1-2.*
Cooper et al., 2015, International Journal of Surgery, vol. 23, p. 211-216.*
Liu et al., 2017, Frontiers in Immunology, vol. 8, article 645, p. 1-6.*
Abkowitz et al., "Mobilization of hematopoietic stem cells during homeostasis and after cytokine exposure," *Blood*, 2003; 102: 1249-53.
Arnold et al., "Hydrogen peroxide mediates the cell growth and transformation caused by the mitogenic oxidase Nox1" *Proc. Natl. Acad Sci USA*, 2001; 98: 5550-5555.
Back et al., "Leukocyte integrin CD11b promoter directs expression in lymphocytes and granulocytes in transgenic mice," *Blood*, 1995; 85: 1017-24.
Banfi et al. "Two novel proteins activate superoxide generation by the NADPH oxidase NOX1," *J. Biol. Chem.*, 2003; 278: 3510-3513.
Banfi et al. "A Mammalian H+ Channel Generated Through Alternative Splicing of the NADPH Oxidase Homolog NOH-1" *Science*, 2000; 287: 138-142.
Barese et al. "Granulocyte colony-stimulating factor prior to nonmyeloablative irradiation decreases murine host hematopoietic stem cell function and increases engraftment of donor marrow cells," *Stem Cells*, 2007; 25(6)1578-85.

(Continued)

*Primary Examiner* — Shin Lin Chen

(57) ABSTRACT

The invention relates to a method of treating chronic granulomatous disease through Hematopoietic stem cell (HSC) transplantation. The method comprises the steps of administering stem cell mobilization agent to human such that the target stem cell population migrates from host niches into the subject's blood. The target stem cells are removed from blood and administering the therapeutic stem cells to human and said therapeutic stem cells are engineered to express $gp91^{phox}$. The steps are repeated multiple times i.e. at least four times. The mobilization agents used in the invention are granulocyte-colony stimulating factor and AMD3100. The method of HSC transplantation is effective in treatment of chronic granulomatous disease.

4 Claims, 17 Drawing Sheets
Specification includes a Sequence Listing.

(56) References Cited

OTHER PUBLICATIONS

Bjorgvinsdottir et al. "Retroviral-Mediated Gene Transfer of gp91 phox Into Bone Marrow Cells Rescues Defect in Host Defense Against Aspergillus fumigatus in Murine X-Linked Chronic Granulomatous Disease" *Blood*, 1997; 89: 41-48.
Blum, "A null mutation in TGF-alpha leads to a reduction in midbrain dopaminergic neurons in the substantia nigra," *Nat Neurosci*, 1998; 1: 374-77.
Brenner and Malech, "Current developments in the design of onco-retrovirus and lentivirus vector systems for hematopoietic cell gene therapy," *Biochim Biophys Acta*, 2003; 1640: 1-24.
Cheng et al. "Homologs of gp91phox: cloning and tissue expression of Nox3, Nox4, and Nox5," *Gene*, 2001; 269: 131-140.
Clark et al.," NADPH oxidase of human neutrophils. Subcellular localization and characterization of an arachidonate-activatable superoxide-generating system," *J. Biol. Chem*, 1987; 262: 4065-74.
Clark, "The Human Neutrophil Respiratory Burst Oxidase," *J. Infect. Dis*, 1990; 161: 1140-1147.
Clarke and Gordon, "Myeloid-specific gene expression" *J. Leukoc. Biol*. 1998; 63: 153-168.
Czechowicz et al. "Efficient transplantation via antibody-based clearance of hematopoietic stem cell niches," *Science* 2007; 318(5854): 1296-99.
Dinauer et al. "Long-Term Correction of Phagocyte NADPH Oxidase Activity by Retroviral-Mediated Gene Transfer in Murine X-Linked Chronic Granulomatous Disease," *Blood*, 1999; 94:914-922.
Dinauer et al. "Variable correction of host defense following gene transfer and bone marrow transplantation in murine X-linked chronic granulomatous disease," *Blood*, 2001; 97:3738-3745.
Dziennis et al., "The CD11b Promoter Directs High-Level Expression of Reporter Genes in Macrophages in Transgenic Mice," *Blood*, 1995; 85: 319-329.
Fedorov et al., "Generation dependent reduction of tTA expression in double transgenic NZL-2/tTA$^{CMV}$ mice," *Genesis*, 2001; 31: 78-84.
Galimi and Verma, "Opportunities for the use of lentiviral vectors in human gene therapy" *Curr. Top Microbiol. Immunol*. 2002; 261: 245-254.
Geiszt et al., "Proteins Homologous to p47$^{phox}$ and p67$^{phox}$ Support Superoxide Production by NAD(P)H Oxidase 1 in Colon Epithelial Cells," *J. Biol. Chem.*, 2003; 278: 20006-20012.
Goebel and Dinauer, "Retroviral-Mediated Gene Transfer and Nonmyeloablative Conditioning: Studies in a Murine X-Linked Chronic Granulomatous Disease Model," *J. Pediatr. Hematol. Oncol.*, 2002; 24: 787-790.
Goldblatt and Thrasher, "Chornic Granulomatous Disease" *Clin Exp. Immunol.*, 2000; 122: 1-9.
Hahn et al., "Correction of murine galactosialidosis by bone marrow-derived macrophages overexpressing human protective protein/ cathepsin A under control of the colony-stimulating factor-1 receptor promoter," *PNAS USA*, 1998; 95: 14880-85.
Ho and Blum, "Induction of Interleukin-1 Associated with Compensatory Dopaminergic Sprouting in the Denervated Striatum of Young Mice: Model of Aging and Neurodegenerative Disease," *J. Neurosci*, 1998; 18: 5614-29.
Horwitz et al. "Treatment of chronic granulomatous disease with nonmyeloablative conditioning and a T-cell-depleted hematopoietic allograft.," *N. Engl. J. Med.*, 2001; 344: 881-888.
Hubner et al.,"Derivation of oocytes from mouse embryonic stem cells," *Science*, 2003; 300: 1251-56.
Imren et al., "Permanent and panerythroid correction of murine β thalassemia by multiple lentiviral integration in hematopoietic stem cells," *Proc Natl Acad Sci USA*, 2002; 99: 14380-14385.
International Preliminary Report on Patentability in application No. PCT/US2017/049815, dated Mar. 5, 2019.
International Search Report and Written Opinion in application No. PCT/US2017/049815, dated Nov. 3, 2017.
Jackson et al.,"The p47phox mouse knock-out model of chronic granulomatous disease," *J. Exp. Med.*, 1995; 182: 751-58.

Jiang et al., "Pluripotency of mesenchymal stem cells derived from adult marrow," *Nature*, 2002; 418: 41-49.
Kang et al. "Chronic granulomatous disease: overview and hematopoietic stem cell transplant," *Journal of Allergy and Clinical Immunology*, 2011; 127(6): 1319-1326.
Kondo et al., "Biology of hematopoietic stem cells and progenitors: implications for clinical application," *Annu Rev. Immunol.*, 2003; 21: 759-806.
Koostra and Verma, "Gene therapy with viral vectors," *Annu Rev Pharmacol. Toxicol*, 2003; 43: 413-439.
Kume and Dinauer, "Gene therapy for chronic granulomatous disease" *J. Lab Clin Med*. 2000, 135: 122-128.
Lakshman and Finn, "Neutrophil disorders and their management" *J. Clin. Pathol*. 2001, 54: 7-19.
Lapidot and Petit, "Current understanding of stem cell mobilization: the roles of chemokines, proteolytic enzymes, adhesion molecules, cytokines, and stromal cells," *Exp. Hematol*, 2002; 30: 973-81.
Lekstrom-Himes and Gallin, "Immunodeficiency diseases caused by defects in phagocytes," *N. Engl. J. Med.*, 2000; 343: 1703-1714.
Li et al. "Multiple PU.1 sites cooperate in the regulation of p40 phox transcription during granulocytic differentiation of myeloid cells," *Blood*, 2002; 99: 4578-4587.
Li et al. "Critical Flanking Sequences of PU.1 Binding Sites in Myeloid-specific Promoters" *J. Biol. Chem*. 1999; 274-32453-32460.
Li et al. "Transcriptional Regulation of the p67$^{phox}$ Gene Role of AP-1 In Concert With Myeloid-Specific Transcription Factors," *J. Biol. Chem*. 2001; 39368-39378.
Li et al., "PU.1 Is Essential for p47phox Promoter Activity in Myeloid Cells," *J. Biol. Chem*. 1997; 272: 17802-17809.
Li et al., "Synthetic muscle promoters: activities exceeding naturally occurring regulatory sequences" *Nat. Biotechnol.*, 1999; 17: 241-245.
Malech, "Progress in Gene Therapy for Chronic Granulomatous Disease," *J. Infect Dis*., 1999, 179 Suppl 2: S318-325.
Malik, "Retroviral-mediated gene expression in human myelomonocytic cells: a comparison of hematopoietic cell promoters to viral promoters," *Blood*, 1995; 86; 2993-3005.
Mardiney and Malech, "Enhanced engraftment of hematopoietic progenitor cells in mice treated with granulocyte colony-stimulating factor before low-dose irradiation: implications for gene therapy," *Blood*, 1996 87(10): 4049-56.
Mardiney et al., "Enhanced host defense after gene transfer in the murine p47phox-deficient model of chronic granulomatous disease," *Blood*, 1997; 89: 2268-75.
May et al. "Therapeutic haemoglobin synthesis in beta-thalassaemic mice expressing lentivirus-encoded human beta-globin," *Nature*, 2000; 406: 82-86.
Miller, "Progress Toward Human Gene Therapy," *Blood*, 1990; 76: 271-78.
Miyoshi et al.,"Development of a Self-Inactivating Lentivirus Vector," *J. Virol*. 1998; 72: 8150-8157.
Naldini, "In Vivo Gene Delivery by Lentiviral Vectors," *Thromb. Haemost*, 1999; 82: 552-554.
Pan et al. "Biodistribution and toxicity studies of VSVG-pseudotyped lentiviral vector after intravenous administration in mice with the observation of in vivo transduction of bone marrow," *Mol. Ther.*, 2002; 6: 19-29.
Papayannopoulou, "Current mechanistic scenarios in hematopoietic stem/progenitor cell mobilization," *Blood*, 2004; 103: 1580-85.
Pawliuk et al., "Correction of sickle cell disease in transgenic mouse models by gene therapy," *Science*, 2001; 294: 2368-2371.
Persons and Nienhuis, "Gene therapy for the hemoglobin disorders: past, present, and future," *Proc Natl Acad Sci USA*, 2000; 97: 5022-24.
Ravin et al. "CRISPR-Cas9 gene repair of hematopoietic stem cells from patients with X-linked chronic granulomatous disease," *Science Translational Medicine*, 2017; 9(372): 1-10.
Rex et al."Normal and Deficient Neutrophils Can Cooperate to Damage Aspergillus fumigatus Hyphae," *J. Infect. Dis*, 1990; 162: 523-528.

(56) References Cited

OTHER PUBLICATIONS

Rhoades et al., "Analysis of the role of AML1-ETO in leukemogenesis, using an inducible transgenic mouse model" *Blood*, 2000; 96: 2108-15.

Roberts et al., "Transcription of the Human Colony-Stimulating Factor-1 Receptor Gene Is Regulated by Separate Tissue-Specific Promoters," *Blood*, 1992; 79: 586-593.

Roesler et al., "Third-generation, self-inactivating gp91phoxlentivector corrects the oxidase defect in NOD/SCID mouse-repopulating peripheral blood-mobilized CD34+ cells from patients with X-linked chronic granulomatous disease," *Blood*, 2002; 100: 4381-4390.

Sato et al. "Novel interferon-based pre-transplantation conditioning in the treatment of a congenital metabolic disorder," *Blood*, 2013; 121(16): 3267-73.

Sclimenti et al., "An extrachromosomal tetracycline-regulatable system for mammalian cells," *Nucleic Acids Res.*, 2000; 28:E80.

Segal et al. "Genetic, biochemical, and clinical features of chronic granulomatous disease" *Medicine* (Baltimore), 2000; 79: 170-200.

Seger et al. "Treatment of chronic granulomatous disease with myeloablative conditioning and an unmodified hemopoietic allograft: a survey of the European experience, 1985-2000" *Blood*, 2002; 100: 4344-4350.

Shariatmadari et al., "Improved technique for detection of enhanced green fluorescent protein in transgenic mice," *Biotechniques*, 2001; 30: 1282-85.

Shivdasani and Orkin, "The Transcriptional Control of Hematopoiesis" *Blood*, 1996; 87: 4025-4039.

Suh et al. "Cell transformation by the superoxide-generating oxidase Mox1," *Nature*, 1999; 401: 79-82.

Suzuki et al. "PU.1 as an essential activator for the expression of gp91phox gene in human peripheral neutrophils, monocytes, and B lymphocytes" *Proc. Natl. Acad Sci USA*, 1998; 95: 6085-6090.

Takahashi et al., "Induction of pluripotent stem cells from mouse embryonic and adult fibroblast cultures by defined factors" *Cell*, 2006; 126: 663-76.

Takeya et al. "Novel human homologues of p47phox and p67phox participate in activation of superoxide-producing NADPH oxidases" *J. Biol. Chem.*, 2003; 25: 25.

Tenen et al., "Transcription factors, normal myeloid development, and leukemia," *Blood*, 1997; 90: 489-519.

Vigna et al., "Robust and efficient regulation of transgene expression in vivo by improved tetracycline-dependent lentiviral vectors." *Mol. Ther.*, 2002; 5: 252-261.

Vowells et al., "Flow cytometric analysis of the granulocyte respiratory burst: a comparison study of fluorescent probes," *J. Immunol. Methods*, 1995; 178: 89-97.

Ward et al., "Regulation of granulopoiesis by transcription factors and cytokine signals," *Leukemia*, 2000; 14: 973-990.

Wilson et al., "Retrovirus-mediated transduction of adult hepatocytes" *PNAS* 1988; 85(9): 3014-18.

Winkelstein et al. "Chronic granulomatous disease. Report on a national registry of 368 patients," *Medicine* (Baltimore) 2000, 79(3): 155-169.

Woods et al., "Development of gene therapy for hematopoietic stem cells using lentiviral vectors," *Leukemia*, 2002; 16: 563-569.

Wright et al., "Physiological Migration of Hematopoietic Stem and Progenitor Cells," *Science* 2001; 294: 1933-36.

Xue et al. "Antibody targeting KIT as pretransplantation conditioning in immunocompetent mice," *Blood*, 2010; 116:5419-22.

Yam et al., "Design of HIV vectors for efficient gene delivery into human hematopoietic cells" *Mol. Ther.*, 2002; 5: 479-484.

\* cited by examiner

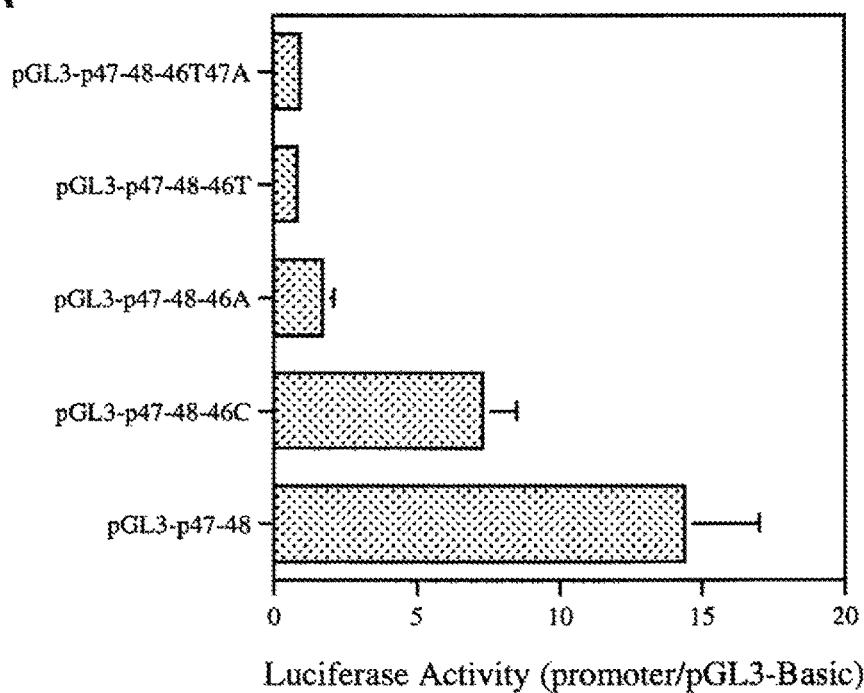
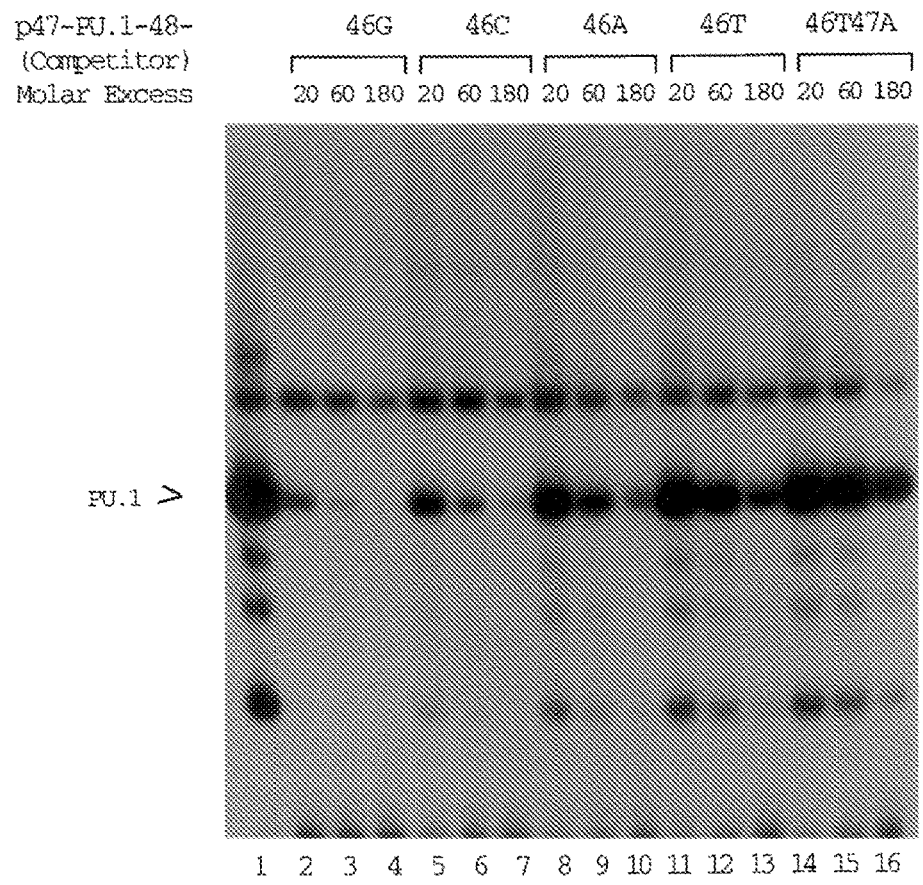
FIG. 4

A

```
-106 GTCCACTTCCTCAATTTCTGTGCAGCTGGGAGGTGAGGTAAGAGGAAGTG
          PU.1a                                PU.1b
- 56 TGGGCCACAGGCTAGGCCCAGAGAGCCTGGAGGAGGAGCCTCTGCCAGAC

-  6 TGGAGAGAAGCAGGCTGAGCCTCCCCAAAGGCAGCTCCTGGGGACTCCC

+ 45 AGGACCACAGGCTGAGACGAGACGCAGGGTGGCTGGAGGAAGTGAGAGGT
                                                PU.1c
+ 95 GAACTCAGCCTGGGACTGGCTGGGCGAGACTCTCCACCTGCTCCCTGGGA

+145 CCATCGCCACCATG
```

B

```
PU.1a Wild type (Wt)   5'-GAGGGTCCACTTCCTCAATTTCTGTG-3'
      Mutant (Mt)      5'-GAGGGTCCACTTGGTCAATTTCTGTG-3'

PU.1b Wild type (Wt)   5'-GGTGAGGTAAGAGGAAGTGTGGGCCA-3'
      Mutant (Mt)      5'-GGTGAGGTAAGACCAAGTGTGGGCCA-3'

PU.1c Wild type (Wt)   5'-AGGGTGGCTGGAGGAAGTGAGAGGTG-3'
      Mutant (Mt)      5'-AGGGTGGCTGGACCAAGTGAGAGGTG-3'
```

FIG. 8

METHODS AND COMPOSITIONS FOR TREATING CHRONIC GRANULOMATOUS DISEASE

PRIORITY CLAIM

This application is a national phase application under 35 U.S.C. § of International Application No. PCT/US2017/049815, filed Sep. 1, 2017 which claims the benefit of priority to U.S. Provisional Application No. 62/382,872, filed Sep. 2, 2016, all of which are hereby incorporated by reference in their entirety.

BACKGROUND

Chronic granulomatous disease (CGD) is an inherited disorder of host defense, in which the generation of superoxide and derivative microbicidal oxidants by the NADPH oxidase in phagocytic leukocytes is absent or markedly deficient due to mutations in oxidase subunit $gp91^{phox}$, $p47^{phox}$ or others. Victims suffer from recurrent and often life-threatening bacterial and fungal infections beginning in early childhood. Chronic inflammatory granulomas, a hallmark of CGD, can obstruct internal organs such as ureter and bowel. Although daily administration of prophylactic antibiotics plus thrice-weekly interferon-γ decreases the frequency of infection and allogeneic bone marrow transplantation from HLA-matched donors cures selected patients, the mortality rates are still 2-4% annually. Because CGD results from specific gene defects in hematopoietic stem cells (HSCs), and mouse models that recapitulate the human disease have been developed, CGD has become an attractive target disorder for gene therapy.

Current methods for treating deficient leukocyte function include bone marrow transplantation, antibiotic and antimycotic prophylaxis, and cytokine therapy. Although bone marrow transplantation has been well developed for several years, its application is still restricted because bone marrow cell donors with a matching genotype are not available in many cases. Furthermore, recipients are at the risk of graft versus host disease (GvHD) and may acquire severe infections during transplantation. Gene therapy involves the introduction of foreign DNA sequences that replace the defective DNA structure of host cells. However, this treatment is still hampered by the complications including malignant transformation and insufficient therapeutic gene expression. Due to safety concerns, clinical trials of gene therapy are being cautiously pursued.

Currently, cytokine therapy is only applied to a few diseases. Such therapies often fail to sufficiently restore the function of cells expressing mutant proteins and are very costly. In addition, because the deficient or mutant genes are often expressed only at specific sites, such as in blood cells, severe side-effects may occur when the drugs are administered systemically.

There is a need for additional compositions and methods for treating chronic granulomatous disease (CGD).

SUMMARY

Hematopoietic stem cell (HSC) transplantation (HSCT), which is also called bone marrow transplantation, is a proven and often curative treatment for a variety of inherited blood/immune disorders, including chronic granulomatous disease (CGD). Increasing the range of HSCT cell sources, especially genetically corrected autologous HSC, is expected to dramatically expand HSCT-based therapies. However, broader applications of HSCT have been limited by the necessary but harmful cytotoxic pre-transplant conditioning (performed with chemotherapy and/or irradiation). Scientists and physicians have been searching for a non-cytotoxic preparative conditioning regimen, without success. Recently a non-toxic and gentle pre-conditioning method has been developed. The inventors contemplate that the new HSCT can be used in the clinic safely with significant therapeutic efficacy for treating CGD as well as other blood/immune disorders. Certain embodiments are directed to performing HSCT therapy on patients who have HLA-matched donors. A further embodiment is directed to genetically engineering the patient's own HSCs to let their progeny express corrected genes. Certain embodiments are directed to an intervention that treats CGD.

Certain embodiments of the invention provide methods for non-cytotoxic HSCT. Non-cytotoxic HSCT includes methods that do not use chemotherapy or irradiation to condition the subject prior to administration of transplant or replacement cells. In certain aspects, the HSCT methods described herein includes administering a stem cell mobilization agent to stimulate migration of target stem cells out of a stem cell niche in the bone marrow, followed by the administration of exogenous (e.g., transplant or replacement) stem cells that subsequently migrate to the appropriate stem cell niche. As used herein exogenous stem cells refers to stem cells other than those stem cells occupying the stem cell niche at the time of mobilization. Thus, exogenous stem cells include stem cells previously isolated from the same patient and returned to that same patient at a later time. In certain aspects this mobilization and transplantation cycle is performed for a number of cycles. In a further aspect the mobilization/transplantation cycle is performed at least four times.

As used herein, a "stem cell niche" is a tissue microenvironment where stem cells are found, and the microenvironment interacts with stem cells to regulate stem cell fate. The word 'niche' can be in reference to the in vivo stem cell microenvironment. In the body, stem cell niches maintain stem cells in a quiescent state, but after activation, the surrounding microenvironment actively signals to stem cells to promote either self-renewal or differentiation to form new cells or tissues. Several factors contribute to the characteristics within a particular niche: (i) cell-cell interactions between stem cells, and between stem cells and neighboring cells; (ii) interactions between stem cells and adhesion molecules, extracellular matrix components, growth factors, and cytokines; and (iii) the physiochemical nature of the microenvironment including oxygen tension, pH, ionic strength (e.g., $Ca^{2+}$ concentration) and presence of various metabolites. The mobilization of the target stem cells (the movement from or evacuation of a niche) increases the probability that a transplant or replacement stem cell will occupy the stem cell niche.

The "target stem cell" is defined as an endogenous stem cell that is mobilized, collected, and/or depleted from a subject. A "transplant or replacement stem cell" is a stem cell that is being introduced into a subject. The transplant or replacement stem cell can be a therapeutic stem cell in that it has been conditioned or otherwise modified to be therapeutic to the subject.

Certain embodiments are directed to methods of non-cytotoxic stem cell transplant or replacement comprising: (a) administering at least one stem cell mobilization agent to a subject, wherein a target stem cell population migrates from a host stem cell niche into the subject's circulating blood; (b) removing the mobilized target stem cells from the subject (e.g., apheresis); (c) administering transplant or replacement stem cells to the subject, wherein the transplant or replacement stem cells migrate to and occupy the host stem cell niche; and (d) repeating steps (a)-(c) 2, 3, 4, 5, 6, 7, 8, 9, or more times.

In certain aspects the transplant or replacement stem cells are therapeutic stem cells. In further aspects the therapeutic stem cells are isolated target stem cells that have been manipulated in vitro. In certain aspects therapeutic stem cells are isolated from the subject to be treated. In other aspects therapeutic stem cells are isolated from a heterologous source, i.e., a source or donor that is not the subject to be treated. The term "isolated" refers to a cell, a nucleic acid, or a polypeptide that is substantially free of heterologous cells or cellular material, bacterial material, viral material, and/or culture medium of their source of origin; or chemical precursors or other chemicals when chemically synthesized. A donor can be an autologous, allogeneic, or xenogeneic (a non-genetically identical donor of another species) donor. In certain aspects the therapeutic stem cells are genetically engineered. In certain aspects the transplant or replacement stem cells are from an autologous donor. In a further aspect the transplant or replacement stem cells are from an allogeneic donor. In a still further aspect the transplant or replacement cells are from a xenogeneic donor. In certain aspects the target stem cell is a hematopoietic stem cell. In certain aspects the transplant or replacement stem cell is a hematopoietic stem cell or a hematopoietic stem cell precursor cell.

In certain aspects a mobilization agent can be selected from interleukin-17 (IL-17), AMD3100, granulocyte-colony stimulating factor (G-CSF), Ancestim, anti-sense VLA-4 receptor (e.g., ATL1102, (Antisense Therapeutics Limited)), POL6326, BKT 140, NOX-A12, Natalizumab, sphigosine-1-phosphate (SIP) agonists, hypoxia-inducible factor, and/or other agents known to mobilize stem cells. In certain aspects the mobilization agent is granulocyte-colony stimulating factor. In certain aspects a mobilization agent includes AMD3100. In a further embodiment the subject is administer both G-CSF and AMD3100. In a further aspect the mobilization agent can be administered prior to or during administration of the transplant or replacement stem cells to the subject.

In certain aspects the isolated target stem cells are manipulated by genetically modifying cells isolated from the subject or obtained from a donor. A number of super-myeloid promoters that are up to 50-fold stronger than the currently characterized phagocyte-specific promoters including those present in the CSF-1R and CD11b genes have been developed. A variant of $gp91^{phox}$ ($gp91^{phox}$-T196F) has been developed that is enzymatically super-active, 7-fold over the wild-type protein. In certain aspects cells are genetically engineered by transducing HSC with lentiviral vectors to express levels sufficient for pan-target cell expression of therapeutic genes, while maintaining their stem cell nature.

The terms "individual," "host," "subject," and "patient" are used interchangeably to refer to an animal or person that is the object of treatment, observation and/or experiment. "Animal" includes vertebrates, such as mammals. "Mammal" includes, without limitation, mice, rats, rabbits, guinea pigs, dogs, cats, sheep, goats, cows, horses, primates, such as monkeys, chimpanzees, and apes, and humans. In certain embodiments the subject is a human subject.

The terms "ameliorating," "treating," "treatment," "therapeutic," or "therapy" do not necessarily mean total cure or abolition of the disease or condition. Any alleviation of any undesired signs or symptoms of a disease or condition, to any extent, can be considered amelioration, and in some respects a treatment and/or therapy.

As used herein, the term "progenitor cells" refers to cells that, in response to certain stimuli, can form differentiated cells, such as hematopoietic or myeloid cells. As used herein, "stem" cells are less differentiated forms of progenitor cells. Typically, such cells are often positive for CD34 in humans.

The term "providing" is used according to its ordinary meaning "to supply or furnish for use." In some embodiments, a protein is provided by administering the protein, while in other embodiments, the protein is effectively provided by administering a nucleic acid that encodes the protein or a cell that synthesizes the protein.

Other embodiments of the invention are discussed throughout this application. Any embodiment discussed with respect to one aspect of the invention applies to other aspects of the invention as well and vice versa. Each embodiment described herein is understood to be an embodiment of the invention that is applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 4. Decreases in promoter activity and PU.1 binding avidity by mutations at position 46 of the p47$^{phox}$ promoter[2]. Panel A shows the results of transfection of Thp-1 cells with the wild-type and mutated reporter constructs. Luciferase activity was determined. Data shown are means (±S.E.) of at least four independent experiments. Panel B shows the results of EMSA using the wild-type and mutated DNA. $^{32}$P-Labeled p47-PU.1-48 probe (see FIG. 3A) was incubated with Thp-1 nuclear extract in the absence (lane 1) or presence of graded excesses of wild-type (46G, lanes 2-4) or mutated (46C, lanes 5-7; 46A, lanes 8-10; 46T, lanes 11-13; 46T47A, lanes 14-16) DNA. PU.1> indicates the specific complex.

FIG. 8. Locations of three PU.1 binding sites in the p40$^{phox}$ promoter[4]. Sequence of the proximal promoter region of the p40$^{phox}$ gene. The three PU.1 sites are underlined and labeled PU.1a, PU.1b, and PU.1c. The arrow indicates the reported transcription start site and the translation initiation codon is double-underlined. (SEQ ID NO: 26-32)

DESCRIPTION

Figure 1:
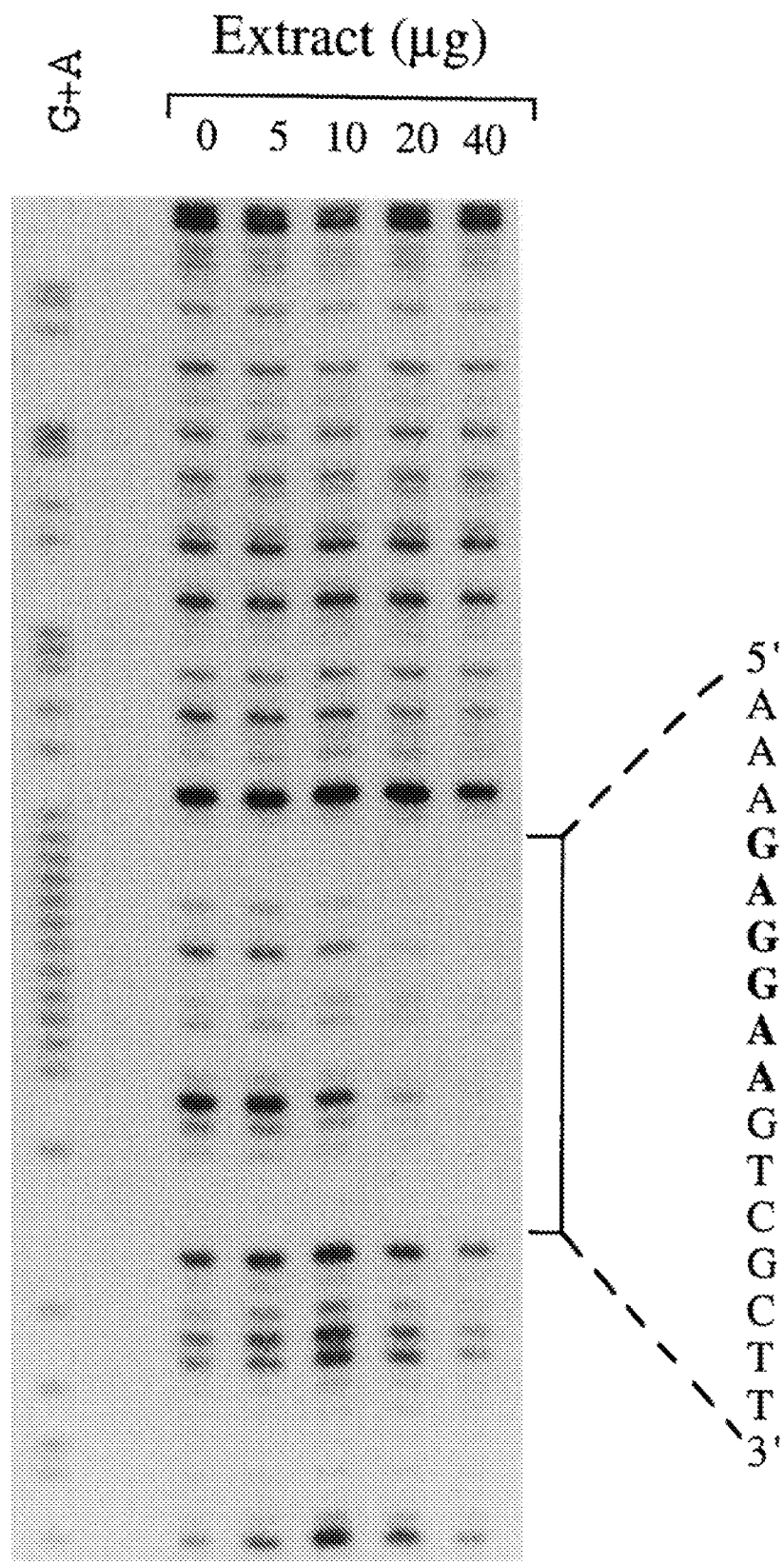
FIG. 1. DNase-I footprint analysis of the p47$^{phox}$ proximal promoter[1]. Labeling of the p47$^{phox}$ genomic DNA fragment (SEQ ID NO: 9) extending from −86 to +52 was carried out by Mlu I digestion of pGL3-p47-86 and followed by filling the recessed 3' termini with [α-$^{32}$P]CTP and DNA polymerase I Klenow fragment. After excision by HindIII digestion and gel purification, the end-labeled probe was subjected to Maxam-Gilbert sequencing reaction (indicated by G+A) or DNase I digestion in the presence of 0, 5, 10, 20, or 40 μg of HL-60 nuclear extract. The sequence (lower strand) of the protected region is shown on the right with the PU.1 consensus motif in bold font.

Hematopoietic stem cell transplantation (HSCT) is used in the treatment of a variety of hematological, autoimmune, and malignant diseases. HSCT is the transplantation of blood stem cells derived from the bone marrow (in this case known as bone marrow (BM) transplantation), blood (such as peripheral blood and umbilical cord blood), or amniotic fluid. Currently, patients endure a harsh conditioning regimen prior to HSCT known as myeloablation to eradicate the disease and hematopoietic stem cells (HSCs). "Myeloablation" refers to the severe or complete depletion of HSCs by the administration of chemotherapy and/or radiation therapy prior to HCST. This treatment severely impacts the myeloproliferative function of the hematopoietic system. Myeloablation techniques for allogeneic transplants (the transplantation of cells, tissues, or organs to a recipient from a genetically non-identical donor of the same species) can include a combination of cyclophosphamide with busulfan or total body irradiation (TBI). Autologous transplants (the transplantation of cells, tissues, or organs to a recipient from a genetically identical donor, e.g., the subject is both the recipient and the donor) may also use similar regimens. Various chemotherapy and/or radiation combinations can be used depending on the disease.

The indiscriminate destruction of HSCs can lead to a reduction in normal blood cell counts, such as lymphocytes, neutrophils, and platelets. Such a decrease in white blood cell counts also results in a loss of immune system function and increases the risk of acquiring opportunistic infections. Neutropenia resulting from chemotherapy and/or radiation therapy may occur within a few days following treatments. The subject remains vulnerable to infection until the neutrophil counts recover to within a normal range. If the reduced leukocyte count (leukopenia), neutrophil count (neutropenia), granulocyte count (granulocytopenia), and/or platelet count (thromboocytopenia) become sufficiently serious, therapy must be interrupted to allow for recovery of the white blood cell and/or platelet counts.

There are "non-myeloablative" conditioning regimens being tested using lower dose chemotherapy and/or radiation therapy that do not eradicate all of the hematopoietic cells, but the subjects still suffer similar side effects, just to a lesser degree. Notably, the treatment of non-malignant diseases by autologous HSCT does not require cytotoxic conditioning regimens. For example, current experimental non-myeloablative conditioning regimens include antibody-based (Czechowicz et al. *Science.* 2007, 318(5854):1296-99; Xue et al. *Blood.* 2010, 116:5419-22), type I interferon-mediated (Sato et al. *Blood.* 2013, 121(16):3267-73), and G-CSF-modulated pre-transplant conditioning (Mardiney and Malech, *Blood.* 1996, 87(10):4049-56; Barese et al. *Stem Cells.* 2007, 25(6)1578-85). However, the antibody-mediated conditioning regimen (Czechowicz et al.) works only in immune-deficient subjects, not for HSCT recipients that are immune-competent. Type I interferon-mediated and G-CSF-modulated pre-transplant conditioning regimens still require irradiation or chemotherapy, but at reduced (non-myeloablative) doses. AMD3100 was tried without irradiation and chemotherapy and shown not to be sufficiently effective. Embodiments of methods described herein provide an effective "non-cytotoxic" regimen (i.e., a regimen with little to no cytotoxicity) so that the side effects of irradiation and chemotherapy are avoided.

I. TREATMENT OF CHRONIC GRANULOMATOUS DISEASE (CGD)

Chronic granulomatous disease (CGD) is a rare inherited disorder in which superoxide generation by the phagocyte NADPH oxidase is absent or markedly deficient. CGD can result from a defect in any of the four phox subunit genes, with 60%-80% of cases due to the X-linked $gp91^{phox}$ deficiency, one-third of cases due to the autosomal recessive $p47^{phox}$ deficiency, and ~2%-3% each due to the autosomal recessive $p22^{phox}$ deficiency or $p67^{phox}$ deficiency (Malech, *J Infect Dis,* 179 Suppl 2: S318-325, 1999; Kume and Dinauer, *J Lab Clin Med,* 135: 122-128, 2000; Winkelstein et al., Medicine (Baltimore), 79: 155-169, 2000). Victims suffer from recurrent and often life-threatening bacterial and fungal infections. CGD is also characterized by abnormally exuberant inflammatory responses leading to granuloma formation, manifested by granulomatous enteritis, genitourinary obstruction, and poor wound healing (Seger et al., *Blood,* 100: 4344-4350, 2002; Lakshman and Finn, *J Clin Pathol,* 54: 7-19, 2001; Winkelstein et al., Medicine (Baltimore), 79: 155-169, 2000). While daily administration of prophylactic oral antibiotics and thrice-weekly administration of prophylactic subcutaneous interferon-γ have been demonstrated to decrease the frequency of infection, CGD continues to be associated with significant morbidity and mortality, with a current mortality of two deaths per 100 patient years. Patients with CGD often die in childhood or in young adult years. Few patients survive beyond 40 years of age. CGD occurs with a frequency of 4-5 per million, appearing to affect all ethnic and racial populations. Whereas the X-linked form affects only males, the autosomal recessive forms affect males and females equally. Female carriers of the X-linked form of CGD are mosaics for the CGD phenotype (Segal et al., Medicine (Baltimore), 79: 170-200, 2000; Lakshman and Finn, *J Clin Pathol,* 54: 7-19, 2001; Malech, *J Infect Dis,* 179 Suppl 2: S318-325, 1999; Kume and Dinauer, *J Lab Clin Med,* 135: 122-128, 2000).

Infusion of granulocytes from allogeneic donors is an important adjuvant to treatment of severe infection in CGD patients. However, using a flow cytometric method to measure oxidase-normal granulocytes in the circulation following infusion of allogeneic granulocytes, Dr. Malech's group at NIH found typically a level of a few percent at one hour and then much lower levels, for example <1% by 6 to 12 hr after infusion. In addition, the rapid development of anti-HLA immune responses limits the usefulness of this treatment. Immediate sequestration and destruction of infused allogeneic granulocytes might occur when they were from a less than perfectly matched donor to an alloimmunized recipient (Malech, *J Infect Dis,* 179 Suppl 2: S318-325, 1999).

CGD can be cured by identically matched sibling allogeneic bone marrow transplant, but the difficulty of finding good matches and the considerable morbidity and mortality associated with allogeneic transplantation have made this treatment an impractical option for most patients. Since bone marrow transplantation has the potential to cure CGD, this satisfies an important criterion for a disease potentially treatable with gene transfer into the hematopoietic stem cells that give rise to granulocytes and monocytes (Horwitz et al., *N Engl J Med,* 344: 881-888, 2001; Seger et al., *Blood,* 100:4344-4350, 2002; Malech, *J Infect Dis,* 179 Suppl 2:S318-325, 1999; Kume and Dinauer, *J Lab Clin Med,* 135:122-128, 2000).

Because CGD results from a single-gene defect in hematopoietic stem cells, and mouse models of CGD have been developed that recapitulate the human disease, CGD has become an attractive target disease for hematopoietic cell gene replacement therapy. Autologous marrow transplantation provides an opportunity for the ex vivo introduction of normal genes into hematopoietic stem cells, using retroviruses or other vector systems, for the correction of genetic diseases. Autologous marrow transplantation avoids complications of allogeneic marrow transplantation, such as graft-versus-host disease (Malech, *J Infect Dis,* 179 Suppl 2:S318-325, 1999; Kume and Dinauer, *J Lab Clin Med,* 135:122-128, 2000; Malech et al., *Proc Natl Acad Sci USA,* 94:12133-12138, 1997; Dinauer et al., *Blood,* 94:914-922, 1999; May et al., *Nature,* 406:82-86, 2000).

CGD is considered as a good candidate for gene therapy by correction of autologous hematopoietic stem cells for additional reasons. Clinical observations suggest that even low percentages of normal circulating neutrophils can provide significant protection against infection. Female carriers of the X-linked form of CGD are mosaics for the CGD phenotype. Some of these carriers have only 5% to 10% of their neutrophils capable of superoxide generation yet show no apparent increase in infections, although others experience recurrent bacterial infections similar to those seen in classic CGD. An important laboratory observation is that when normal and CGD neutrophils are mixed, a small amount of the hydrogen peroxide released extracellularly by normal cells diffuses into CGD cells, partially restoring microbicidal activity (Rex et al., *J Infect Dis,* 162:523-528, 1990). Thus, one would expect a "bystander effect" to magnify the relative impact of provision of even very small numbers of oxidase-positive granulocytes to CGD patients. However, it must be pointed out that because the in vivo expression of a transgene (~20% of normal in corrected CGD cells) is much lower than that of endogenous genes, the proportion of corrected cells required for effective correction of CGD phenotype must be higher than the number of normal cells present in the CGD carriers (Malech, *J Infect Dis,* 179 Suppl 2:S318-325, 1999; Kume and Dinauer, *J Lab Clin Med,* 135:122-128, 2000; Dinauer et al., *Blood,* 97:3738-3745, 2001; Goebel and Dinauer, *J Pediatr Hematol Oncol,* 24:787-790, 2002).

All patients with $p47^{phox}$-deficient and $p67^{phox}$-deficient forms of CGD have a protein-null phenotype, as do the vast majority of patients with $p22^{phox}$-deficient and $gp91^{phox}$-deficient CGD. Thus, in considering gene therapy for most patients with this disorder, the potential of a dominant negative effect of an abnormal protein on the ability of the normal gene to correct the abnormality need not be considered. However, some patients with X-linked CGD have point mutations in the $gp91^{phox}$ open reading frame that result in production of normal amounts of a non-functional protein. The same has been reported in rare patients with $p22^{phox}$-deficient CGD. Although a dominant negative effect on the product of a therapeutic gene is a theoretical limitation in these patients, this has not yet proven to be a significant issue (Malech, *J Infect Dis,* 179 Suppl 2: S318-325, 1999; Kume and Dinauer, *J Lab Clin Med,* 135: 122-128, 2000).

Recombinant retroviral vectors were first shown in the early 1980s to be capable of transferring a functional gene into murine bone marrow cells. However, the application of this technology to the treatment of CGD and other hematologic diseases in patients has been more difficult than originally anticipated. Although protocols have been developed for efficient retroviral transduction of long-lived, transplantable murine HSCs, only low rates (0 to 5%) of gene transfer have been seen in comparable studies with large animal models (dogs, primates) and in human clinical trials. The difficulty in transducing non-human HSCs appears to result from limiting factors such as the inability of current retroviral vectors to integrate into non-dividing cells and a paucity of viral receptors on HSCs. In the past several years, a number of laboratories have reported marked improvements in stem cell transduction in large animal models because of optimization by cytokines, use of "activated" stem cells, alternative retroviral envelopes, and transduction in the presence of a fibronectin fragment, which co-localizes retroviruses and target cells, thus increasing the efficiency of viral transduction (Kume and Dinauer, *J Lab Clin Med,* 135: 122-128, 2000; Brenner and Malech, *Biochim Biophys Acta,* 1640: 1-24, 2003; Galimi and Verma, *Curr Top Microbiol Immunol,* 261: 245-254, 2002; Bjorgvinsdottir et al., *Blood,* 89: 41-48, 1997). In a phase I clinical trial of ex vivo gene therapy of $p47^{phox}$-deficient CGD, prolonged production (2-6 months) of a low number (1 in 5000) of oxidase-normal neutrophils was achieved (Malech et al., *Proc Natl Acad Sci USA,* 94: 12133-12138, 1997). In mice with $gp91^{phox}$-deficient CGD (X-CGD), correction of approximately 20% of cellular NADPH oxidase activity in 50% to 80% of neutrophils was obtained and shown to be protective against *Aspergillus fumigatus*-induced pneumonia (Dinauer et al., *Blood,* 94:914-922, 1999; Bjorgvinsdottir et al., *Blood,* 89:41-48, 1997). However, full protection against the major pathogens requires better expression of the therapeutic genes and greater numbers of oxidant-generating phagocytes. Partial correction of cellular enzymatic activity may not be sufficient to restore full microbicidal and host defense functions (Dinauer et al., *Blood,* 97: 3738-3745, 2001).

A. Phagocyte NADPH Oxidase

Polymorphonuclear neutrophils and macrophages constitute the first line of host defense against many pathogenic bacteria and fungi (Clark, *J Infect Dis,* 161: 1140-1147, 1990). Their ability to kill invading microorganisms depends to a large extent on superoxide and derivative microbicidal oxidants generated by NADPH oxidase (also referred to as respiratory burst oxidase). The superoxide-generating NADPH oxidase is a coordinated assembly of the membrane-associated heterodimeric flavocytochrome $b_{558}$ ($gp91^{phox}$ plus $p22^{phox}$) with four cytosolic factors, $p67^{phox}$, $p47^{phox}$, $p40^{phox}$, and a small Rho-family GTP-ase (Rac1 or Rac2) (Segal et al., *Medicine* (Baltimore), 79:170-200, 2000; Goldblatt and Thrasher, *Clin Exp Immunol,* 122:1-9, 2000). Upon activation of the oxidase in response to physiologic stimuli such as phagocytosis, the cytoplasmic subunits $p47^{phox}$, $p67^{phox}$, and $p40^{phox}$ translocate to the membrane-bound cytochrome. NADPH is oxidized to NADP$^+$, and electrons are transported down a reducing potential gradient to flavin adenine dinucleotide (FAD) and then to two non-identical heme groups. On the vacuolar or extracellular side of the membrane, the final step in the electron transport chain occurs when two molecules of diatomic oxygen each accept an electron and are converted to superoxide anion. The net equation involves the reduction of two molecules of $O_2$ to two molecules of superoxide anion ($O_2$—) at the expense of one molecule of NADPH. Superoxide, a relatively weak microbicidal oxidant, is then metabolized to the more toxic hydrogen peroxide, hypohalous acids (bleach in the neutrophil), and hydroxyl anion by other reactions (Segal et al., *Medicine* (Baltimore), 79:170-200, 2000; Clark et al. *J Biol Chem,* 262:4065-4074, 1987; Horwitz et al., *N Engl J Med,* 344:881-888, 2001; Seger et al., *Blood,* 100:4344-4350, 2002; Lakshman and Finn, *J Clin Pathol,* 54:7-19, 2001; Lekstrom-Himes and Gallin, *N Engl J Med,* 343:1703-1714, 2000). Whereas $p22^{phox}$ is ubiquitously expressed, $gp91^{phox}$, $p47^{phox}$, $p67^{phox}$, and $p40^{phox}$ exhibit myeloid-specific expression, which is controlled to a large extent by the myeloid transcription factor PU.1 (Suzuki et al., *Proc Natl Acad Sci USA,* 95:6085-6090, 1998; Li et al., *J Biol Chem,* 272:17802-17809, 1997; Li et al., *J Biol*

Chem, 274:32453-32460, 1999; Li et al., *J Biol Chem*, 276:39368-39378, 2001; Li et al., *Blood*, 99:4578-4587, 2002). B-cells contain all of the components of the phagocyte NADPH oxidase, and generate superoxide upon stimulation with various agonists, but at a far lower level than neutrophils, perhaps due to lower levels of the phox proteins. However, several non-phagocytic cells such as endothelial cells, fibroblasts, and renal mesangial cells contain NADPH oxidase-like components and can generate low levels of superoxide anion. Very recently, a number of homologs of the membrane-bound core enzyme subunit gp91$^{phox}$ have been identified. Members of this family of NADPH oxidase (NOX) proteins have a different tissue distribution from gp91$^{phox}$ (Cheng et al., *Gene*, 269:131-140, 2001). One member, NOX1, is expressed predominantly in the epithelial cells of the gut, particularly the colon (Arnold et al., *Proc Natl Acad Sci USA*, 98: 5550-5555, 2001; Suh et al., *Nature*, 401: 79-82, 1999; Banfi et al., *Science*, 287: 138-142, 2000). Of great interest are the recent reports describing homologues of p67$^{phox}$ and p47$^{phox}$ (NOXA1 and NOXO1, respectively) which like NOX1 are expressed in the gut epithelial cells (Banfi et al., *J Biol Chem*, 278:3510-3513, 2003; Geiszt et al., *J Biol Chem*, 278:20006-20012, 2003; Takeya et al., *J Biol Chem*, 25:25, 2003). These co-factors interact with NOX1 in an unknown manner to stimulate both constitutive and agonist-induced superoxide. Interestingly, initial studies suggest that the levels of superoxide generated by the human NOX1 system are far less than those seen with the phagocyte system, suggesting that the function of NOX1/NOXA1/NOXO1 may not necessarily be that of host defense.

B. Lentiviral Vectors in Hematopoietic Gene Therapy:

The major challenges in gene therapy have been delivery of DNA to the target cells and duration and level of expression. Retroviral vectors integrate into target cell chromatin and have therefore been the primary system developed for HSC gene transfer, since integration into the host genome is absolutely required in order to pass the transgene to progeny cells. Disabled murine retroviruses such as the Moloney murine leukemia virus (MLV) were the initial systems developed. Advantages include the now extensive safety record for these vectors, ease of vector production due to the ability to isolate stable producer cell lines, lack of toxicity to target cells, and stable integration of vector sequences. However, the requirement for passage of the target cell through the M-phase of the cell cycle to permit nuclear entry of standard murine retroviral vectors may explain poor gene transfer efficiency to largely quiescent HSCs (Brenner and Malech, *Biochim Biophys Acta*, 1640: 1-24, 2003). However, just a few years of experience with lentiviral vectors, suggest that these vectors may offer an exciting alternative, and accumulating data indicate that this gene delivery system may well represent a breakthrough in the field (Brenner and Malech, *Biochim Biophys Acta*, 1640:1-24, 2003; Galimi and Verma, *Curr Top Microbiol Immunol*, 261:245-254, 2002; Miyoshi et al., *J Virol*, 72:8150-8157, 1998; Naldini, *Thromb Haemost*, 82:552-554, 1999; Pan et al., *Mol Ther*, 6:19-29, 2002; Yam et al., *Mol Ther*, 5:479-484, 2002; Kootstra and Verma, *Annu Rev Pharmacol Toxicol*, 43:413-439, 2003). Lentivirus belongs to the complex retrovirus group and can infect both dividing and non-dividing cells by integration into the target genome. Furthermore, lentivector provirus present in engrafted transduced HSC is less subject to silencing over the long term in vivo than are the murine oncoretroviral vectors. Third generation lentivectors exhibit both a high degree of biosafety (equal or superior to that of MLV-based vectors) and outstanding performance (up to 99% transfection efficiency in HSC) (Pawliuk et al., *Science*, 294:2368-2371, 2001; Woods et al., *Leukemia*, 16:563-569, 2002; Kondo et al., *Annu Rev Immunol*, 21:759-806, 2003). Permanent and pan-erythroid correction of murine β-thalassemia has been achieved by multiple lentiviral integration (three proviral copies per genome) in hematopoietic stem cells (Imren et al., *Proc Natl Acad Sci USA*, 99:14380-14385, 2002). The transduction was sustained for >7 months in both primary and secondary transplants, at which time approximately 95% of the red blood cells in all mice contained human β-globin at therapeutic levels. Similar effectiveness was also obtained in a mouse model of sickle cell disease by erythroid-specific accumulation of the anti-sickling protein mediated by a lentiviral vector (Pawliuk et al., *Science*, 294: 2368-2371, 2001).

Using non-obese diabetic/severe combined immunodeficient (NOD/SCID) mice, Malech demonstrated for the first time that hematopoietic stem cells from patients with X-linked chronic granulomatous disease (X-CGD) give rise to X-CGD-phenotype neutrophils in the NOD/SCID model that can be corrected using VSV-G-pseudotyped, 3rd-generation, self-inactivating (SIN) lentivector (Miyoshi et al., *J Virol*, 72:8150-8157, 1998; Pan et al., *Mol Ther*, 6:19-29, 2002) encoding gp91$^{phox}$ (Roesler et al., *Blood*, 100:4381-4390, 2002). X-CGD patient-mobilized CD34$^+$ peripheral blood stem cells (CD34$^+$PBSCs) were transduced with lentivector-gp91$^{phox}$ or amphotropic oncoretrovirus MFGS-gp91$^{phox}$ and correction evaluated both ex vivo and in vivo in NOD/SCID mice. Only lentivector transduced CD34$^+$ PBSCs under ex vivo conditions that were non-permissive for cell division, but both vectors performed best under conditions permissive for proliferation. Under the latter conditions, lentivector and MFGS achieved significant ex vivo correction of X-CGD CD34+PBSCs (18% and 54% of cells expressing gp91$^{phox}$, associated with 53% and 163% of normal superoxide production, respectively). However, lentivector, but not MFGS, achieved significant correction of human X-CGD neutrophils arising in vivo in NOD/SCID mice that underwent transplantation (20% and 2.4%, respectively). Thus, 3rd-generation SIN lentivector-gp91$^{phox}$ provides significant correction of the X-CGD functional defect in oxidase activity and efficiently transduces NOD/SCID-repopulating X-CGD CD34+PBSCs, resulting in long-term persistence of gp91$^{phox}$ expression in human X-CGD neutrophils in vivo. Nevertheless, it was pointed out that the expression of gp91$^{phox}$ protein per cell from the lentivector CMV promoter construct was probably inadequate for clinical application. Studies with the K562-X-CGD cell line suggested that the basis for this observation is low mRNA production mediated by the CMV promoter. The substitution of human EF-1a promoter for CMV could enhance correction of the deficiency in gp91$^{phox}$ expression from lentivector (Roesler et al., *Blood*, 100:4381-4390, 2002).

C. Synthetic Promoters:

In studies on the role of transcription factor/cis-element integration in gene regulation, tandem repetitive cis-elements have been successfully used to amplify function. Repetitive regulatory elements have also been engineered into other types of constructs. In the tetracycline-regulated system, expression of the gene of interest is controlled by a promoter that contains seven tetracycline response elements (TRE)(Sclimenti et al., *Nucleic Acids Res*, 28:E80, 2000; Vigna et al., Mol Ther, 5:252-261, 2002). Recently, synthetic muscle promoters have been developed with activity greater than the naturally occurring promoter sequences. Skeletal muscle is an attractive target for somatic gene therapy because of its long life span, ease of accessibility for gene delivery by injection, and large capacity for protein synthesis and secretion. However, relatively low levels of expression from naturally occurring promoters have limited the use of muscle as a gene therapy target. Myogenic-restricted gene promoters display complex organization, usually involving combinations of several myogenic regulatory elements. By random assembly of E-box, MEF-2, TEF-1, and SRE sites into synthetic promoter recombinant libraries, and screening of hundreds of individual clones for transcriptional activity in vitro and in vivo, several artificial promoters were isolated whose transcriptional potencies greatly exceeded those of natural myogenic and viral gene promoters (Li et al., *Nat Biotechnol*, 17: 241-245, 1999).

II. STEM CELL TRANSPLANTATION OR REPLACEMENT

Stem cells are undifferentiated cells that can differentiate into specialized cells and can divide (through mitosis) to produce more stem cells. In mammals, there are two broad types of stem cells: (i) embryonic stem cells, which are isolated from the inner cell mass of blastocysts, and (ii) adult stem cells, which are found in various tissues. In adult organisms, stem cells and progenitor cells act as a repair system for the body, replenishing adult tissues. Usual sources of adult stem cells in humans include bone marrow (BM), adipose tissue (fat cells), and blood. Harvesting stem cells from blood can be done through apheresis, wherein blood is drawn from a donor (similar to a blood donation), and passed through a machine that extracts stem cells and returns other portions of the blood to the donor. Another source of stem cells is umbilical cord blood.

Adult stem cells are frequently used in medical therapies, for example in bone marrow transplantation. Stem cells can now be grown, manipulated, and/or transformed (differentiated) into specialized cell types with characteristics consistent with cells of various tissues such as muscles or nerves. Embryonic cell lines and autologous embryonic stem cells generated through therapeutic cloning have also been proposed as promising candidates for therapies.

Autologous harvesting of stem cells is one of the least risky methods of harvesting. By definition, autologous cells are obtained from one's own body, just as one may bank his or her own blood for elective surgical procedures, one may also bank stem cells. Autologous stem cell transplantation is a medical procedure in which stem cells are removed, stored, and/or reintroduced into the same person. These stored cells can then be the source for transplant or replacement stem cells in the methods described herein.

Stem cell transplants are most frequently performed with hematopoietic stem cells (HSCs). Autologous HSCT comprises the extraction of HSCs from the subject and/or freezing of the harvested HSCs. After conditioning or genetic engineering of cells isolated from the subject, the subject's HSCs are transplanted into the subject. Allogeneic HSCT involves HSC obtained from an allogeneic HSC donor. Typically the allogeneic donor has a human leukocyte antigen (HLA) type that matches the subject.

Embodiments of the non-cytotoxic methods described herein comprise mobilizing a target stem cell population (inducing the movement of the stem cells to the blood or other body fluid); removing, isolating, and/or selecting a the target stem cell population from the stem cell-enriched body fluid; administering a transplant or replacement stem cell population to a subject, wherein the transplant or replacement stem cell population localizes in the niche for the target stem cell population. In certain aspects the steps of the method are repeated a number of times. Multiple rounds of transplantation can lead to an increasing representation of the transplant or replacement stem cell population in the subject.

In certain aspects hematopoietic stem cells are mobilized from their niche in the bone marrow and replaced with a therapeutic stem cell. Hematopoietic stem cells (HSCs) are bone marrow cells with the capacity to reconstitute the entire hematopoietic system. Hematopoietic stem cells are identified by their small size, lack of lineage (lin−) markers, low staining with vital dyes such as rhodamine (rhodamine-DULL, also called rholo), and presence of various antigenic markers on their surface. A number of the HSC markers belong to the cluster of differentiation series, like: CD34, CD38, CD90, CD133, CD105, CD45, and also c-kit (stem cell factor receptor). The hematopoietic stem cells are negative for markers used to detect lineage commitment, and are, thus, called Lin-minus (Lin−). Blood-lineage markers include but are not limited to CD13 and CD33 for myeloid, CD71 for erythroid, CD19 for B lymphocytes, CD61 for megakaryocytes for humans; and B220 (murine CD45) for B lymphocytes, Mac-1 (CD11b/CD18) for monocytes, Gr-1 for granulocytes, Ter119 for erythroid cells, Il7Ra, CD3, CD4, CD5, CD8 for T lymphocytes, etc. in mice. Antibodies can be used to deplete the lin+ cells.

Stem cells can include a number of different cell types from a number of tissue sources. The term "induced pluripotent stem cell" (iPS cell) refers to pluripotent cells derived from mesenchymal cells (e.g., fibroblasts and liver cells) through the over-expression of one or more transcription factors. In certain aspects iPS cells are derived from fibroblasts by the over-expression of Oct4, Sox2, c-Myc, and Klf4 (Takahashi et al. *Cell*, 126:663-76, 2006 for example). As used herein, "cells derived from an iPS cell" refers to cells that are either pluripotent or terminally differentiated as a result of the in vitro culturing or in vivo transplantation of iPS cells.

Neural stem cells are a subset of pluripotent cells that have partially differentiated along a neural cell pathway and express some neural markers, including for example nestin. Neural stem cells may differentiate into neurons or glial cells (e.g., astrocytes and oligodendrocytes).

A population of cells can be depleted of cells expressing certain surface markers using a selection process that removes at least some of the cells expressing various cell surface markers. This selection process may be done by any appropriate method that preserves the viability of the cells that do not express the selection marker, including for example, fluorescence-activated cell sorting (FACS) or magnetically-activated cell sorting (MACS). Preferably, depleted populations contain less than 10%, less than 5%, less than 2.5%, less than 1%, or less than 0.1% of cells expressing the selection marker.

Hematopoietic stem cells reside in specific niches in the bone marrow (BM) that control survival, proliferation, self-renewal, or differentiation. In normal individuals, the continuous trafficking of HSCs between the BM and blood compartments likely fills empty or damaged niches and contributes to the maintenance of normal hematopoiesis (Wright et al. *Science*. 2001, 294:1933-36; Abkowitz et al. *Blood*. 2003, 102:1249-53). It has been known for many years that egress of HSCs can be enhanced by multiple agonists known as "stem cell mobilization agents." The hematopoietic cytokine granulocyte-colony stimulating factor (G-CSF), a glycoprotein that stimulates the bone marrow to produce granulocytes and stem cells and release them into the bloodstream, is widely used clinically to elicit HSC mobilization for BM transplantation (Lapidot and Petit. *Exp. Hematol.* 2002, 30:973-81; Papayannopoulou, T. *Blood.* 2004, 103:1580-85). Functionally, it is a cytokine and hormone, a type of colony-stimulating factor, and is produced by a number of different tissues. In addition, AMD3100 has been shown to increase the percentage of persons that respond to the therapy and functions by antagonizing CXCR4, a chemokine receptor important for HSC homing to the BM. In certain aspects a subject is administered an agent that induces movement of a stem cell from the niche and an agent that inhibits the homing of a stem cell to the niche.

The dosages and dosage regimen in which the mobilization agents are administered will vary according to the dosage form, mode of administration, the condition being treated and particulars of the patient being treated. Accordingly, optimal therapeutic concentrations will be best determined empirically at the time and place through routine experimentation.

Certain mobilization agent(s) may be administered parenterally in the form of solutions or suspensions for intravenous or intramuscular perfusions or injections. In that case, the mobilization agent(s) are generally administered at the rate of about 10 µg to 10 mg per day per kg of body weight. Methods of administration include using solutions or suspensions containing approximately from 0.01 mg to 1 mg of active substance per ml. In certain aspects the mobilization agent(s) are administered at the rate of about 10, 20, 30, 40, 50, 60, 70, 80, 90, or 100 µg to 1, 2, 3, 4, 5, 6, 7, 8, 9, or 10 mg per day per kg of body weight.

Certain mobilization agents may be administered enterally. Orally, the mobilization agent(s) can be administered at the rate of 100 µg to 100 mg per day per kg of body weight. In certain aspects the mobilization agent(s) can be administered at the rate of about 100, 150, 200, 250, 300, 350, 400, 450, or 500 µg to about 1, 5, 10, 25, 50, 75, 100 mg per day per kg of body weight. The required dose can be administered in one or more portions. For oral administration, suitable forms are, for example, tablets, gel, aerosols, pills, dragees, syrups, suspensions, emulsions, solutions, powders and granules.

The agent(s) and/or pharmaceutical compositions disclosed herein can be administered according to various routes, typically by injection, such as local or systemic injection(s). However, other administration routes can be used as well, such as intramuscular, intravenous, intradermic, subcutaneous, etc. Furthermore, repeated injections can be performed, if needed.

For in vivo administration, active agent(s) can be added to, for example, a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the active agent is encapsulated.

In contrast to difficult bone marrow transplants, HSCs can be easily collected from the peripheral blood and this method provides a bigger graft, does not require that the donor be subjected to general anesthesia to collect the graft, results in a shorter time to engraftment, and may provide for a lower long-term relapse rate. In order to harvest HSCs from the circulating peripheral blood, subjects are administered one or more mobilization agents that induce cells to leave their niche and circulate in the blood. The subjects then undergo apheresis to enrich and collect the HSCs and then return the HSC-depleted blood to the subjects.

The compositions can be administered using conventional modes of delivery including, but not limited to, intravenous, intraperitoneal, oral, subcutaneous, intraarterial, and by perfusion through a regional catheter. When administering the compositions by injection, the administration may be by continuous infusion or by single or multiple boluses. For parenteral administration, the stem cell mobilization agents may be administered in a pyrogen-free, parenterally acceptable aqueous solution comprising the desired stem cell mobilization agents in a pharmaceutically acceptable vehicle. A particularly suitable vehicle for parenteral injection is sterile distilled water in which one or more stem cell mobilization agents are formulated as a sterile, isotonic solution, properly preserved.

The methods described herein provide gentle and low-risk, but high-level, replacement of endogenous stem cells with either genetically engineered or conditioned HSCs or combinations thereof.

Cells may be cultured and (i) expanded to increase the population of stem cells, (ii) genetically engineered and/or (iii) otherwise conditioned, prior to reintroduction of such cells into a patient. These stem cells or precursor cells may be used for ex vivo gene therapy, whereby the cells may be transformed (i.e., genetically engineered) in vitro prior to reintroduction of the transformed cells into the patient. In gene therapy, using conventional recombinant DNA techniques, a selected nucleic acid, such as a gene, may be isolated, placed into a vector, such as a viral vector, and the vector transfected into a stem cell, to transform the cell, and the cell may in turn express the product encoded by the gene. The cell then may then be introduced into a patient (Wilson et al. *PNAS.* 1998, 85:3014-18). However, there have been problems with efficient hematopoietic stem cell transfection (Miller. *Blood.* 1990, 76:271-78). A transformed cell can be engineered to express and/or secrete a therapeutic protein such as a growth factor, cytokine, monoclonal antibody (positive modulator of another protein or cell or a negative modulator of another protein or cell), ligand, enzyme, receptor, etc.

Ex vivo administration of active agents can be done by any standard method that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired.

III. EXAMPLES

The following examples, as well as the figures, are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

Example 1

A series of super myeloid promoters (5-50-fold stronger than CSF-1R or CD11b promoters) were selected from a synthetic library. This library was constructed by random ligation of myeloid-specific promoter elements PU.1, C/EBPα, and AML-1 and myeloid-associated promoter elements Sp1 and AP-1, and then splicing them upstream of a mini-myeloid promoter/luciferase vector pGL3-p47-86 that was characterized previously. The successful construction of the library and subsequent screening were based on the promoters of the genes for several components of the phagocyte NADPH oxidase. In addition, a gp91$^{phox}$ variant was generated that has a 7-fold increased level of enzymatic activity compared with the wild-type protein. We are also developing a method to transduce HSC with lentiviral vectors to levels sufficient for pan-target cell expression of therapeutic genes, while maintaining their stem cell nature. Mary Dinauer (Washington University), a consultant on this project, previously created gp91$^{phox}$ knockout mice, a useful model of X-CGD. With this mouse model, she carried out several studies of X-CGD gene therapy and obtained a great deal of critical data in this field.

Figure 2:
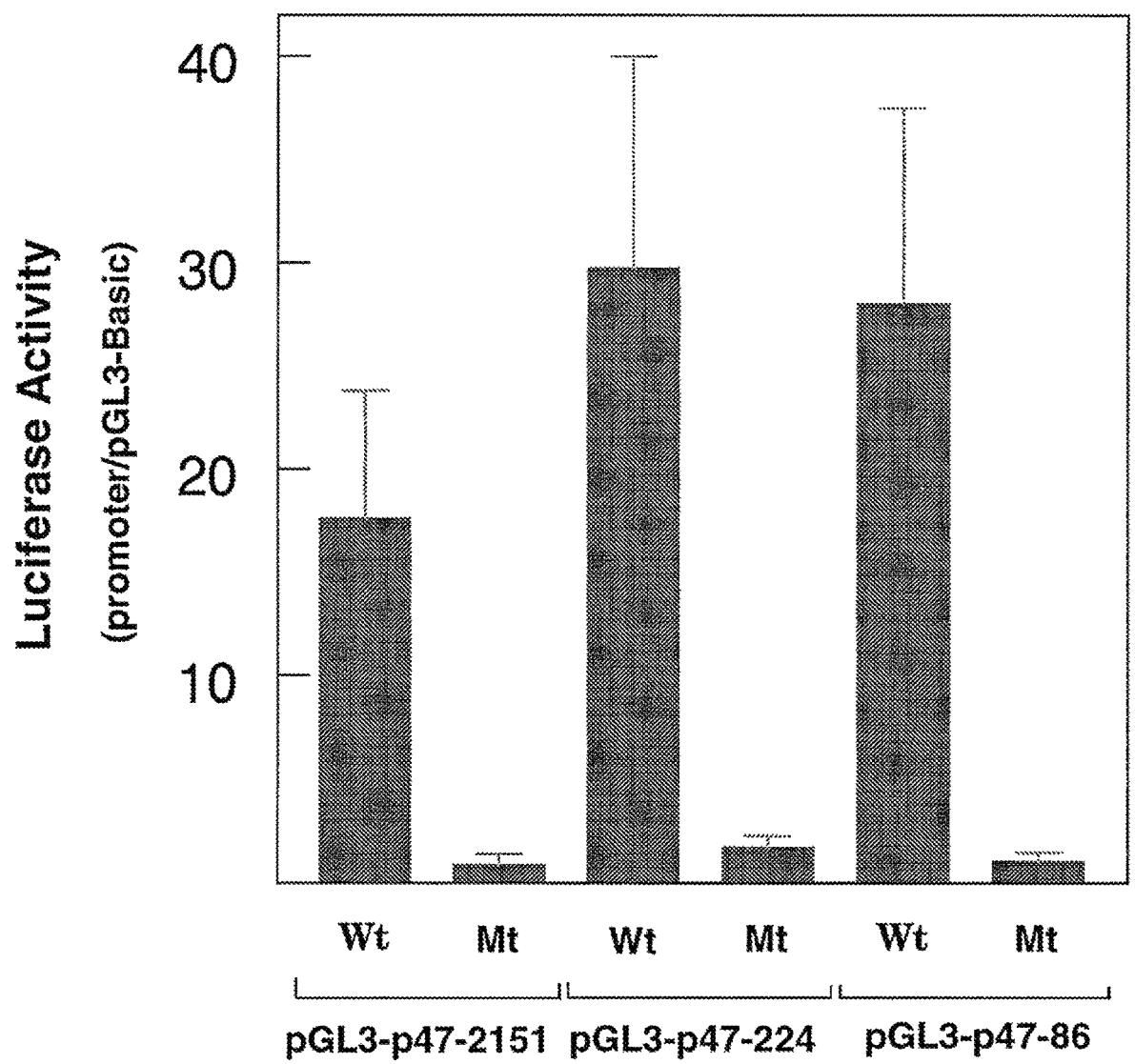
FIG. 2. Mutation of the PU.1 binding site eliminates p47$^{phox}$ promoter activity[1]. Transfection of HL-60 cells, determination of luciferase activity, and expression of results were done as described[1]. The p47$^{phox}$ constructs as indicated were either wild type (Wt) or PU.1 binding site-mutated (Mt). Data (mean±S.E.) shown are from at least four independent experiments.

The PU.1 Binding Site of the p47$^{phox}$ Promoter is Essential for Transcriptional Activity in Myeloid Cells:

The p47$^{phox}$ protein, an essential cytosolic component of the phagocyte NADPH oxidase, is exclusively expressed in macrophages and neutrophils. Primer extension analysis was performed to demonstrate a predominant transcriptional start site (TSS) 21 nucleotides upstream of the translation initiation codon. Transcription of p47$^{phox}$ in HL-60 cells was largely dependent on elements contained in the proximal portion of the 5' flanking region, specifically between positions −36 and −86, relative to the TSS. DNAse I footprint analysis identified a protected region between −37 and −53 that contains a consensus binding site for the myeloid-specific transcription factor PU.1 (FIG. 1). Moreover, this element binds specifically to PU.1 from either myeloid cell nuclear extracts or in vitro synthesis and mutations of the PU.1 site abolished binding and promoter activity (FIG. 2). The promoter was active in a number of myeloid cells, but not in non-myeloid cells, unless a PU.1 expression vector was co-transfected. Thus, p47$^{phox}$ transcription requires PU.1, likely accounting for its limited expression in phagocytic cells.

Figure 3:
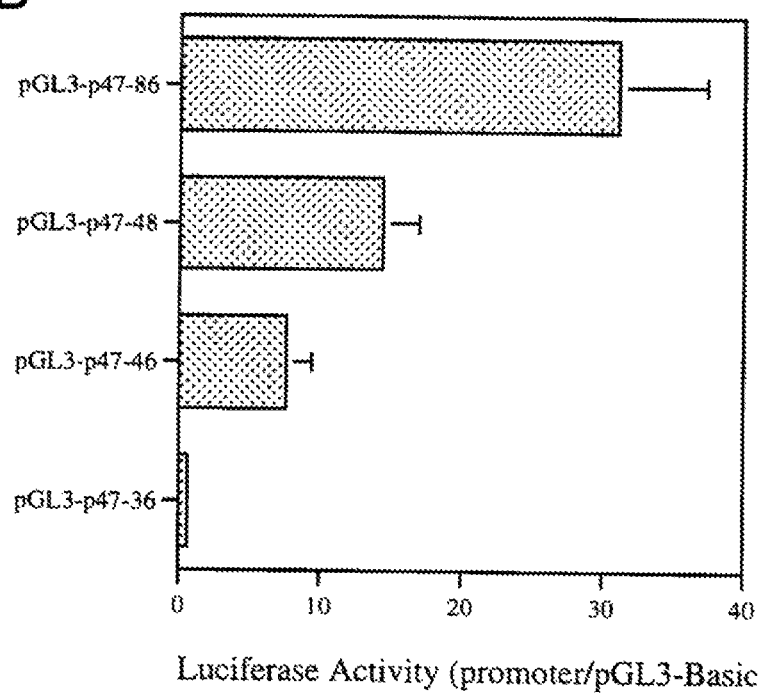
FIG. 3. Functional analysis of the p47$^{phox}$ proximal promoter. Panel A (SEQ ID NO: 10-17) shows partial sequences of the pGL3-p47 reporter constructs. Sequences derived for the p47$^{phox}$ gene are shown in capitals, whereas sequences from the pGL3-Basic vector sequences are in lowercase. Numbers indicate nucleotide positions relative to the transcription start site (TSS) of the p47$^{phox}$ gene. Underlining indicates the sequences used as probes in EMSA. Panel B shows the results of transient transfection assays in THP-1 cells. Luciferase activity was determined 48 hours after transfection and reported relative to the base-line activity of the promoterless construct pGL3-Basic. Values were corrected for transcription efficiency using cotransfection with the Renilla expression plasmid pRL-CMV. The data shown are means (±S.E.) of at least five independent experiments.

Flanking Sequences of PU.1 Binding Sites are Functionally Critical in Monocyte/Macrophage Promoters:

The consensus PU.1 binding sequence (GAGGAA) is located on the lower DNA strand from bp −40 to −45 relative to the p47$^{phox}$ transcriptional start site. Although p47phox promoter-luciferase reporter construct −46 dictates tissue-specific expression, the −86 construct has maximum activity. The role of immediate upstream flanking sequences of the PU.1 binding site was investigated using the human monocyte cell line Thp-1. Although less active than construct −86, construct −48 showed enhanced promoter activity relative to construct −46 (FIG. 3). Mutations at bp −48 had little effect, whereas mutations of nucleotide G at bp −46 and/or T at −47 dramatically reduced both PU.1 binding and promoter activity (FIG. 4). The PU.1 binding avidity of these sequences correlated closely with their capacity to dictate reporter gene transcription. Analogous studies of the promoter of CD18, another PU.1-regulated myeloid-specific gene showed that mutations of the corresponding G and T residues reduced PU.1 binding and nearly abolished promoter activity. The immediate upstream flanking sequences of the PU.1 consensus motif are important and their significant effects on myeloid gene promoter activity are determined by their influences on PU.1 binding avidity. Recent studies show that specific flanking nucleotides both 5' and 3' from the core, as well as core binding residues, form a critical PU.1 binding array.

Figure 5:
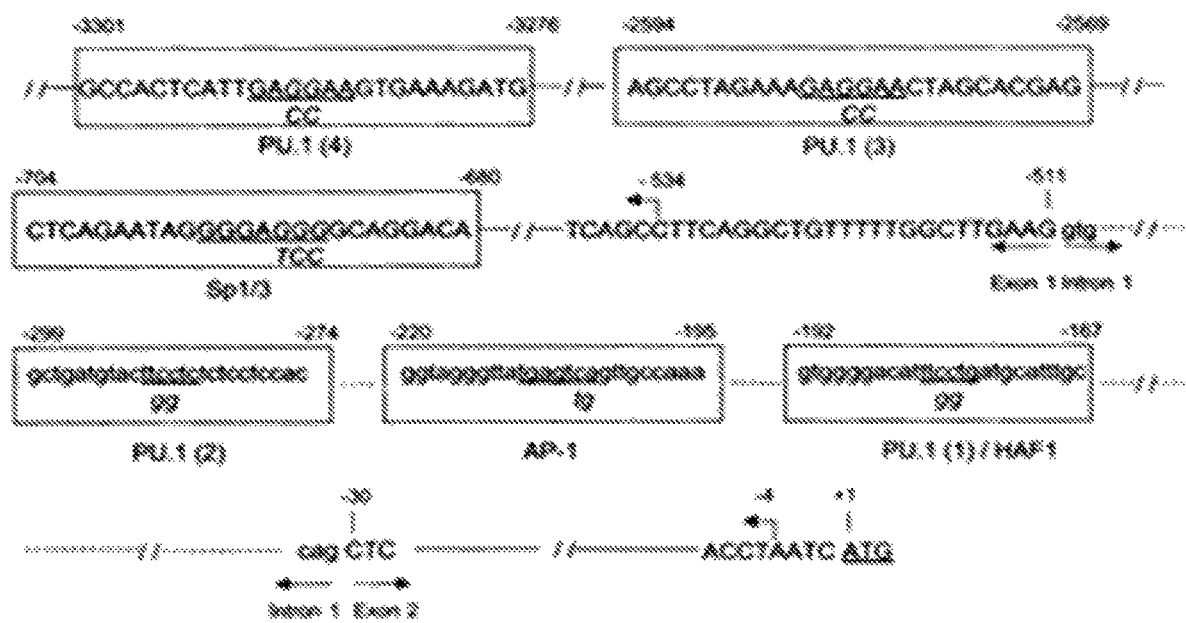
FIG. 5. Location of cis elements in the p67$^{phox}$ promoter[3]. Nucleotides are numbered relative to the adenine (bp+1) in the translation initiation codon (underlined). The intron sequences are indicated by lower case letters and dashed lines, and the exons and upstream promoter sequences are indicated by upper case letters and solid lines. Horizontal arrows indicate the exon/intron boundaries. The identified cis elements are boxed and labeled, and the core consensus sequences are underlined. (SEQ ID NO: 18-25)
Figure 6:
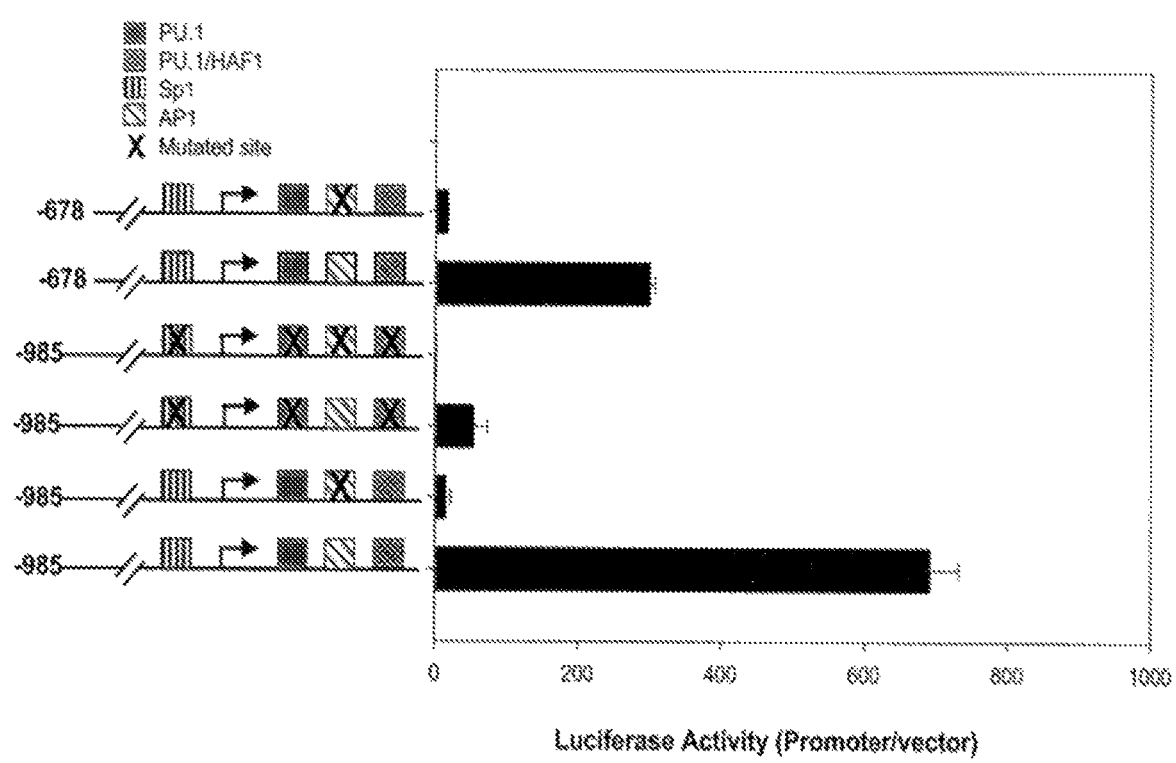
FIG. 6. Among the four active promoter elements, the AP-1 site is essential for the p67$^{phox}$ promoter activity in myeloid cells[3]. Mutation of the AP-1 site alone or in combination with mutations of the PU.1 and Sp1 sites reduces p67$^{phox}$ promoter by >90%. The indicated mutations were introduced into the pGL-p67-678/-4 or pGL-p67-985/-4 constructs by site-directed mutagenesis.
Figure 7:
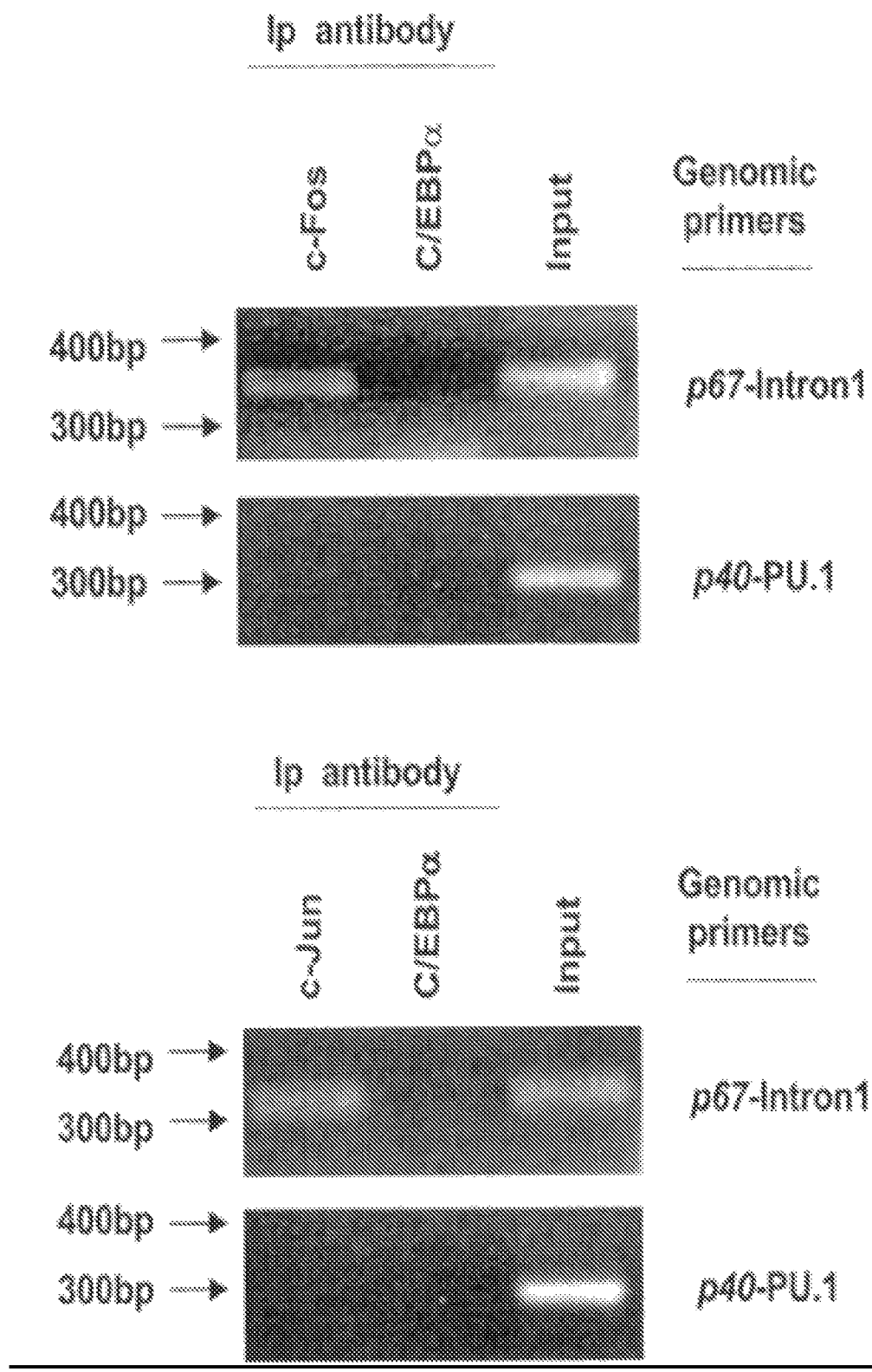
FIG. 7. The AP-1 site in intron 1 of the p67$^{phox}$ gene binds members of the Fos and Jun families of proteins in myeloid cells both in vitro and in vivo[3]. ChIP analysis of the p67$^{phox}$ promoter AP-1 site. Cross-linked HL-60 chromatin was immuno-precipitated with antibodies to c-Fos, c-Jun/AP-1, or C/EBPα or in the absence of antibody (input). The cross-linking was reversed, and the DNA was purified and then analyzed by PCR using specific primers for the AP-1 binding sites of the p67$^{phox}$ promoter (p67-intron 1) or for the p40$^{phox}$ promoter (p40-PU.1) as a control.

Cooperation Between PU.1/HAF1, Sp1, and AP-1 of p67$^{phox}$ Promoter in Phagocytes:

The myeloid-specific transcriptional regulation of p67$^{phox}$ is a component of phagocyte respiratory burst NADPH oxidase. Analysis was carried out on the p67$^{phox}$ 5'-flanking region from −3669 to −4 (relative to ATG), including the first exon and intron and part of the second exon. The construct extending from −985 to −4 produced the highest luciferase activity in myeloid HL-60 cells, but was not active in HeLa or Jurkat cells, indicating myeloid-specific expression. Four active elements were identified: Sp1/Sp3 at −694, PU.1 at −289, AP-1 at −210, and PU.1/HAF1 at −182, the latter three being in the first intron (FIG. 5). These cis elements bound their cognate transacting factors both in vitro and in vivo. Mutation of the Sp1, PU.1, or PU.1/HAF1 site each decreased promoter activity by 35-50%. Mutations in all three sites reduced promoter activity by 90%. However, mutation of the AP-1 site alone nearly abolished promoter activity (FIG. 6). The AP-1 site bound Jun and Fos proteins from HL-60 cell nuclear extract and in the intact cells as demonstrated by chromatin immunoprecipitation (ChIP) assay (FIG. 7). Co-expression with Jun-B in AP-1-deficient cells increased promoter activity. These data showed that full p67$^{phox}$ promoter activity requires cooperation between myeloid-specific and broad transcription factors, with AP-1 being most critical for function.

Figure 9:
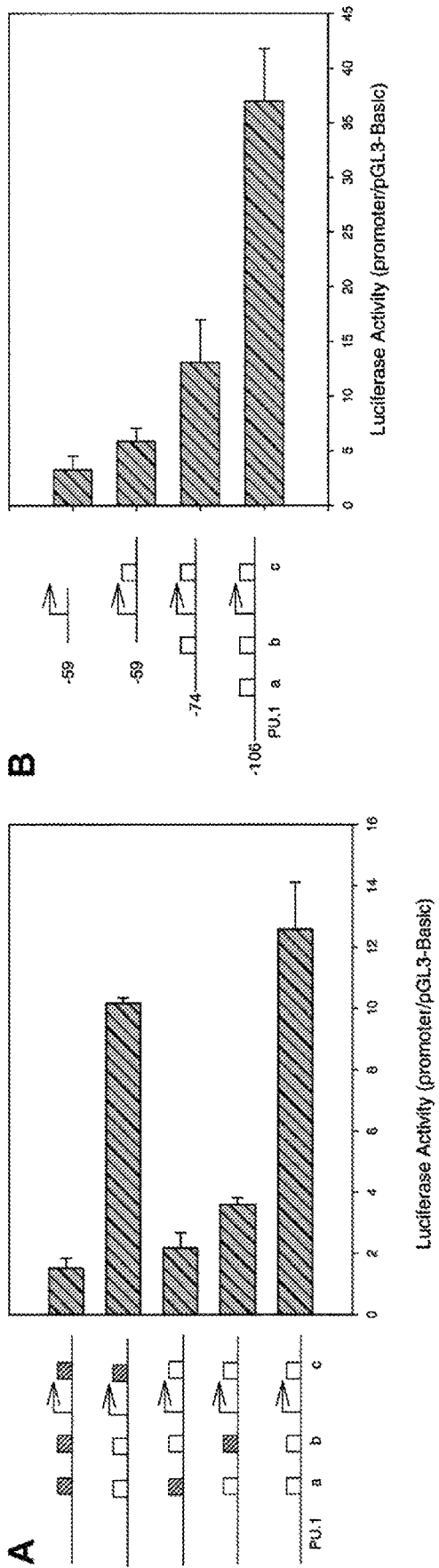
FIG. 9. Effect of three PU.1 sites on p40$^{phox}$ promoter activity in HL-60 cells[4]. The three PU.1 sites (open boxes) present in the pGL3-p40-1599 construct were mutated (hatched boxes) singly or in combination and the resulting constructs assayed for reporter gene activity in HL-60 cells. The arrow indicates the reported transcription start site.

Multiple PU.1 Binding Sites Contribute to the p40$^{phox}$ Promoter Activity:

The p40$^{phox}$ protein, a regulatory component of the phagocyte NADPH oxidase, is preferentially expressed in cells of myeloid lineage. The transcriptional regulation of the p40$^{phox}$ gene in HL-60 myeloid cells was investigated. Deletion analysis of ~6 kb of the 5'-flanking sequence of the gene demonstrated that the proximal 106 bp of the promoter exhibited maximum reporter activity. This region contains three potential binding sites for PU.1 (FIG. 8). Mutation or deletion of each PU.1 site decreased promoter activity and the level of activity mediated by each site correlated with its binding avidity for PU.1, as determined by gel shift competition assays. Mutation of all three sites abolished promoter activity in myeloid cells (FIG. 9). ChIP assays demonstrated occupation of the PU.1 sites by PU.1 in vivo in HL-60 cells. Co-transfection of the pGL3-p40-106 reporter construct with a dominant-negative PU.1 mutant dramatically reduced promoter activity, whereas over-expression of PU.1 increased promoter activity. The p40$^{phox}$ promoter activity and transcript levels were increased in HL-60 cells during DMSO-induced differentiation towards a granulocyte phenotype and this was associated with increased cellular levels of PU.1 protein. In summary, the findings demonstrate that PU.1 binding at multiple sites in the proximal region is required for p40$^{phox}$ gene transcription in myeloid cells.

Figure 10:
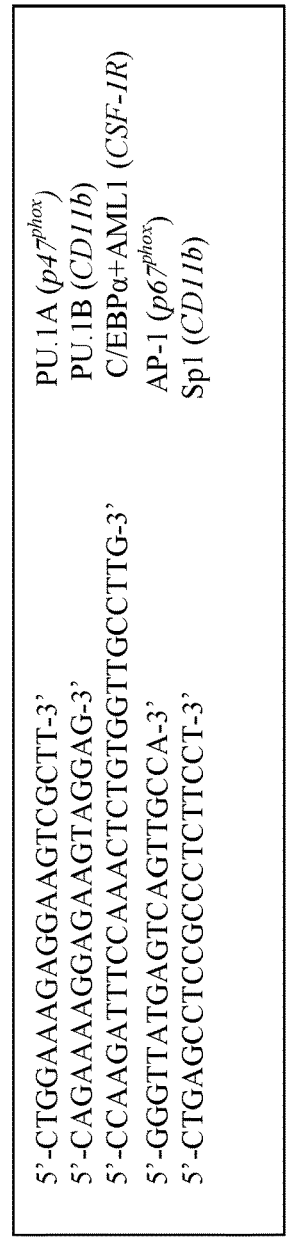
FIG. 10. The oligonucleotide sequences used to make synthetic promoters. Sequences of cis-elements were derived from native myeloid promoters of the genes designated in parentheses (SEQ ID NO: 33-37).
Figure 11:
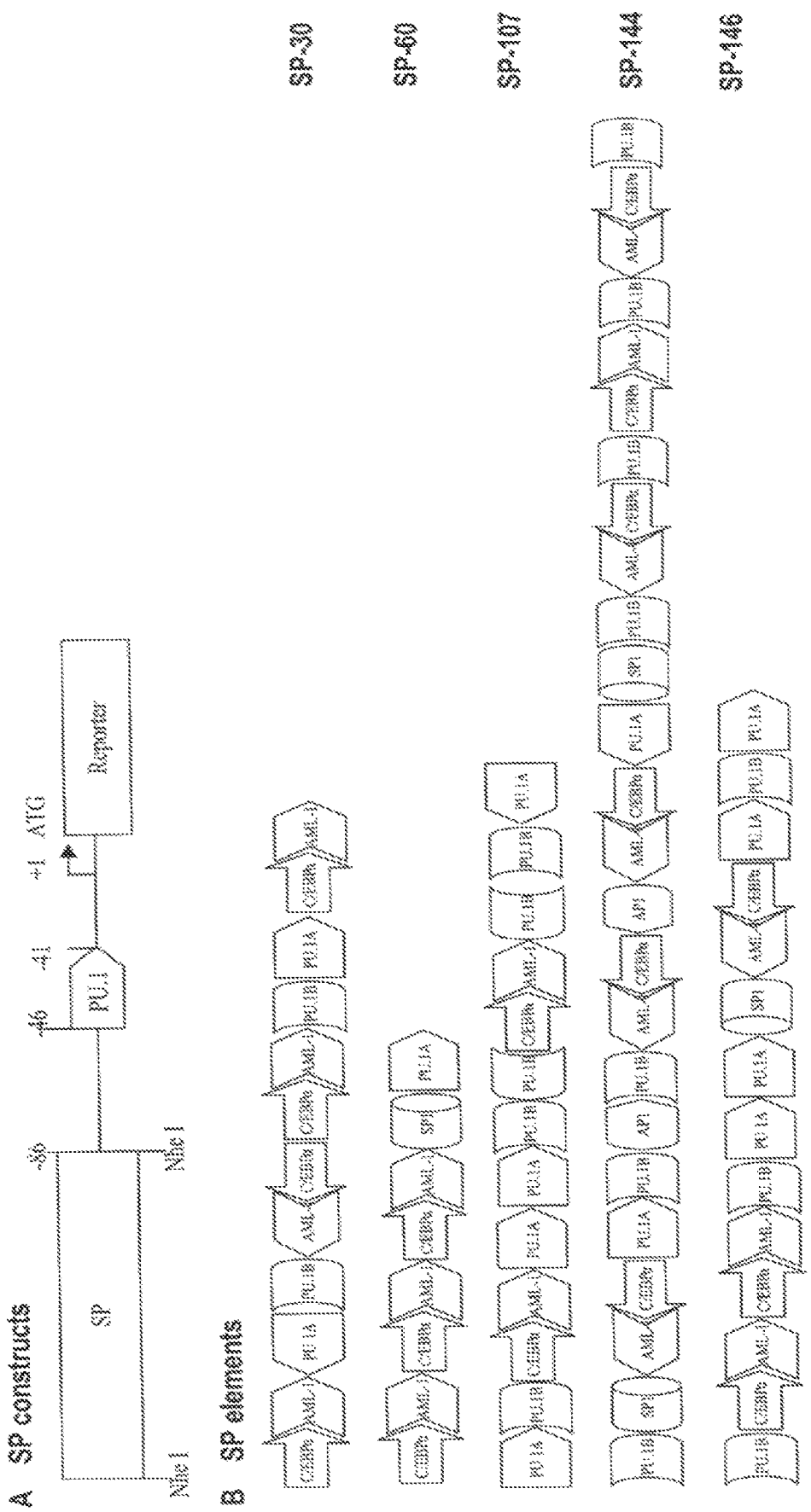
FIG. 11. Design and sequence of synthetic promoters. Synthetic promoter elements in the constructs with the highest in vitro reporter gene activity relative to the basal control pGL3-P47-86.

Construction of a Synthetic Promoter Library:

Myeloid-specific cis promoter elements for PU.1, C/EBPα, and AML-1 and myeloid-associated cis promoter elements for Sp1 and AP-1 (Clarke and Gordon, *J Leukoc Biol*, 63:153-168, 1998; Ward et al., Leukemia, 14:973-990, 2000; Shivdasani and Orkin, *Blood*, 87:4025-4039, 1996;

Tenen et al., *Blood,* 90:489-519, 1997) were chosen for the promoter libraries. There are two different categories of PU.1 binding sites GAGGAA and GGAGAA. Both were chosen and designated as PU.1A and PU.1B, respectively. Native sequences adjacent to the core motif of each cis regulatory element were included to avoid loss of potentially important sequences (FIG. 10). The synthetic promoter element oligonucleotides were 20 or 30 base pairs in length, such that regulatory elements would appear on the same face of the DNA helix when reassembled (FIG. 10). Double-strand oligo-nucleotides of PU.1A, PU.1B, C/EBPα, AML-1, Sp1, and AP-1 promoter elements with a ratio of 2:2:2:2:1:1 were randomly ligated and products were gel separated. DNA fragments 100-500 bp in length were collected and ligated to a NheI linker, which also contained an Sp1 element for protection of CpG islands and also non-island DNA regions from de novo methylation. The resulting DNA was then inserted into the pGL3-p47-86 plasmid at the NheI site to generate synthetic promoter libraries (FIG. 11A).

Screening for Synthetic Promoters with Strong Activity:

To measure the strength of the synthetic promoters, in vitro luciferase activity of more than 200 different clones was assayed in 24-well plates containing transiently transfected human Thp-1 monocytic cells. The cytomegalovirus (CMV) basic promoter was used as a ubiquitous promoter control. PGL3-p47-86 was used as a basal activity control. Thirty-eight independent clones showing promoter activity at least 5-fold higher than the basal control were confirmed by repeating experiments. Ten of these were sequenced (FIG. 11B) and further characterized.

Figure 12:
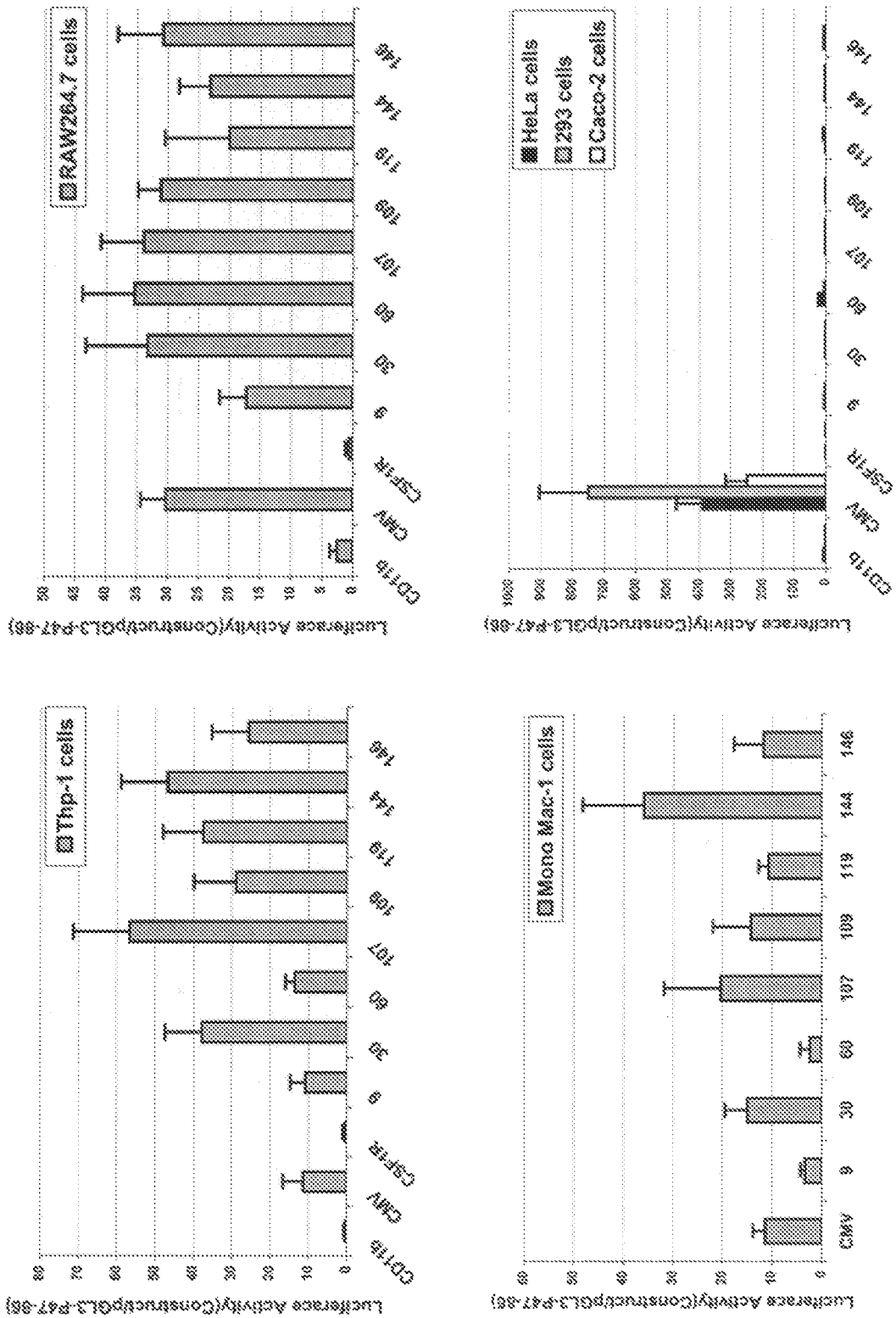
FIG. 12. Dual luciferase analysis of synthetic promoters. Thp-1, RAW264.7, Mono Mac-1, HeLa, 293, and Caco-2 cells were transfected and luciferase activity measured 48 hours later. Synthetic promoters are indicated by clone number.

Myeloid-Specific Activity of the Super-Promoters:

The specificity of the super-promoters was evaluated by transient transfections in several myeloid and non-myeloid cell lines. In human monocytic cell Thp-1, Mono Mac-1, mouse macrophage cell RAW264.7 (FIG. 12), J774, and WEHI-3 (data not shown), luciferase activity of the super-promoters was extremely high, 10-200-fold over that of the CSF1R (Roberts et al., *Blood,* 79:586-593, 1992) or CD11b (Dziennis et al., *Blood,* 85:319-329, 1995) promoters. In contrast, in human intestinal epithelial cell Caco-2, cervix epithelioid carcinoma cell HeLa, embryonic kidney cell 293 (FIG. 12), T lymphocyte Jurkat, and mouse osteoblasts Oct-1 (data not shown), specific luciferase activity of the super-promoters was quite low compared with the CMV promoter.

Figure 13:
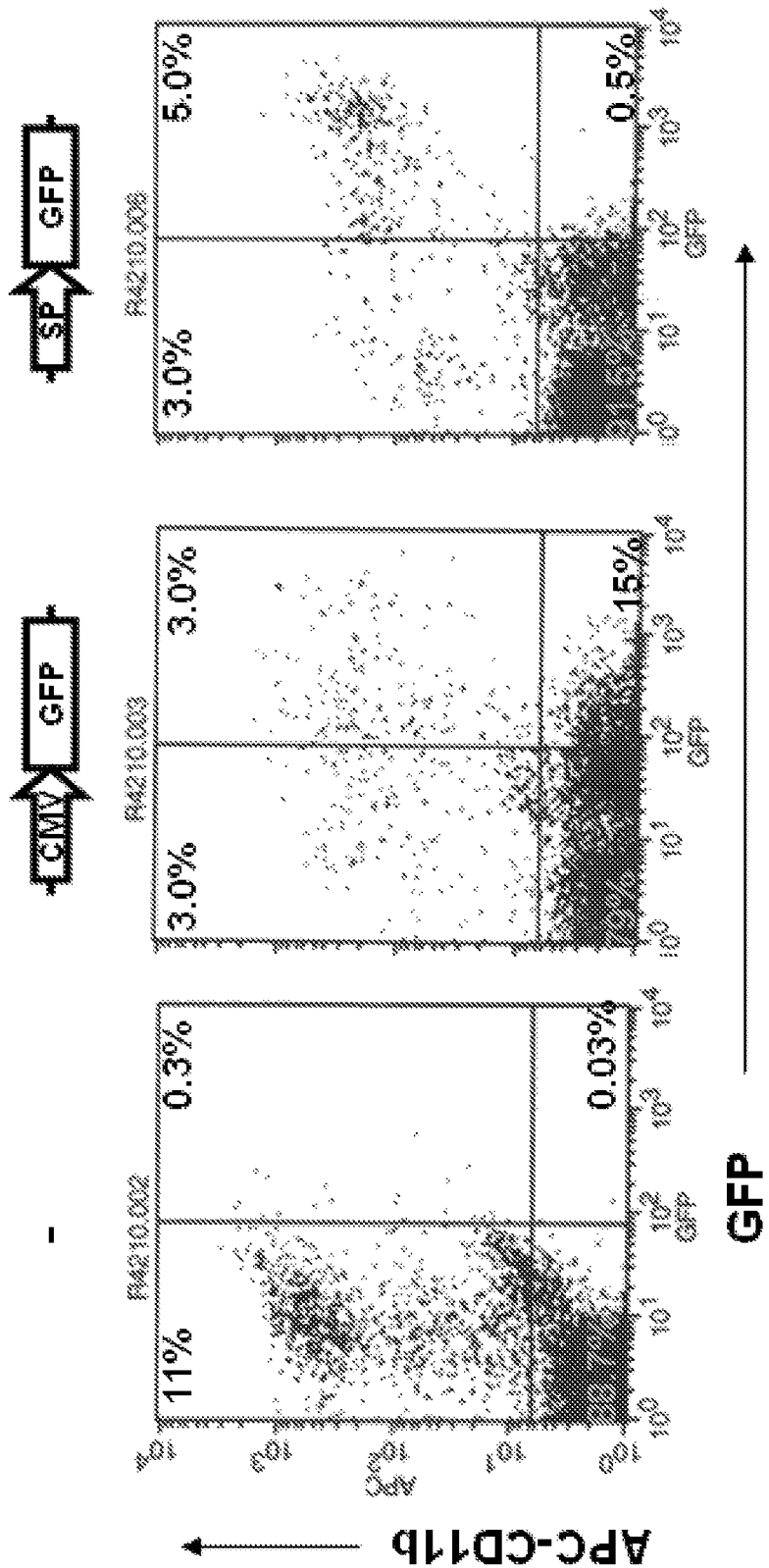
FIG. 13. FACS analysis of transplanted mice. Peripheral leukocytes from BMT recipient mice 2 months post-transplantation of bone marrow ex vivo transduced without (left panel) or with the indicated lentivectors of 0.3×10$^9$ IU/ml at multiplicity of infection (MOI) of ~50 (middle and right panels). CD11b is used as a myeloid marker. C57BL mice have been reported to have a low proportion of PB myeloid cells including neutrophils and monocytes.
Figure 14:
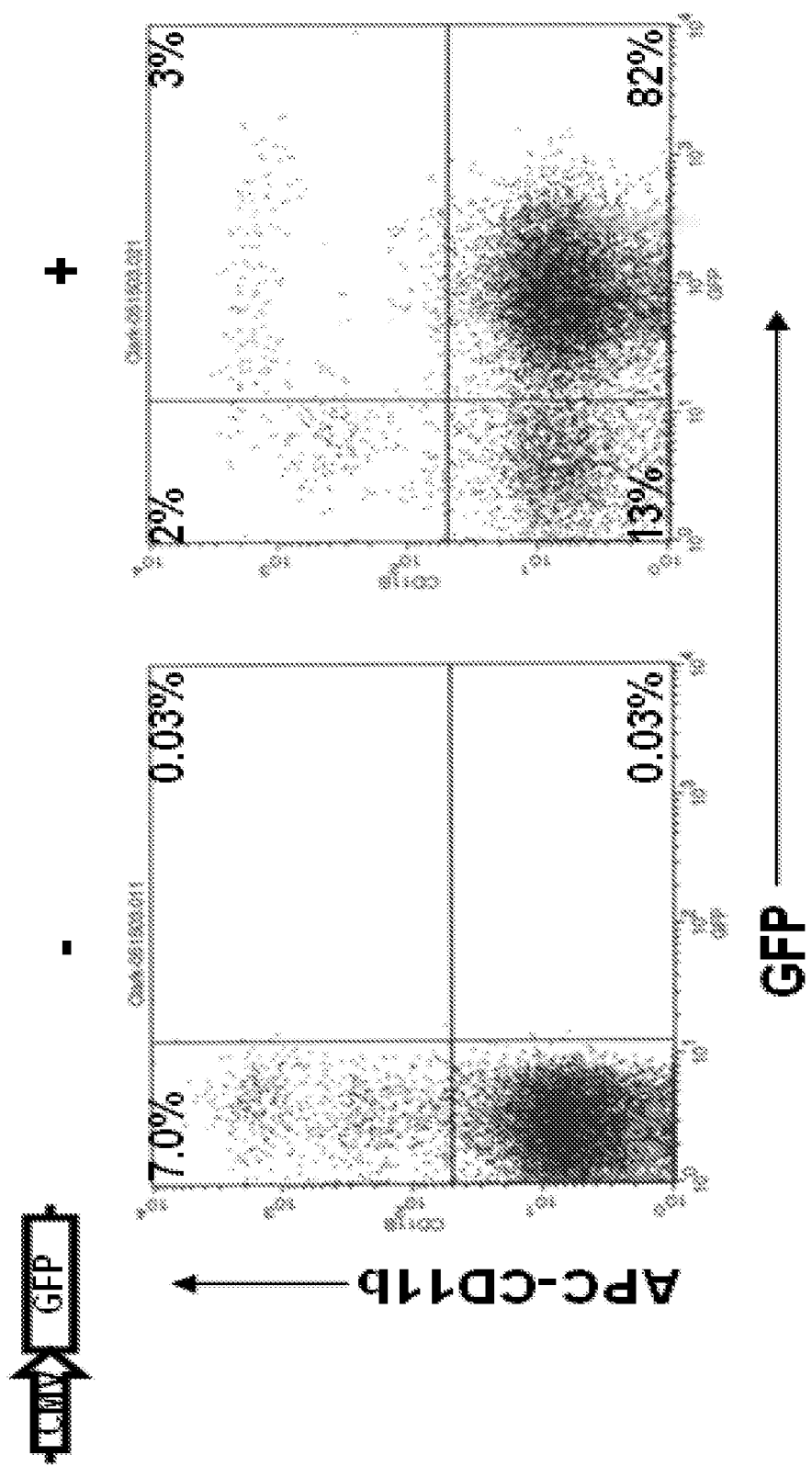
FIG. 14. FACS analysis of transplanted mice. The study was similar to that in FIG. 13. BMT was performed with ex vivo transduced cells without (left panel) or with (right panel) high-titer (1.0×10$^9$ IU/ml) CMV-GFP lentiviral vector at MOI of ~50.

Primary Evaluation of the Super-Myeloid Promoters In Vivo:

In vivo promoter activity was investigated with the use of bone marrow transplantation (BMT). The method of Pawliuk (Pawliuk et al., *Science,* 294:2368-2371, 2001) was adapted to transduce HSC with lentiviral vectors, while leaving their stem cell nature unchanged, to levels of efficiency sufficient for pan-target cell expression of therapeutic genes. Briefly, bone marrow cells were harvested from donor mice, treated with Lympholyte-M to enrich for hematopoietic stem cells, pre-cultured overnight with cytokines, and transduced in 0.85 ml of culture with concentrated lentiviral super-promoter (SP)-EGFP for 6 hours. Approximately $10^6$ cells were transplanted by i.v. injection into lethally irradiated recipient mice. At week 10 post transplantation, GFP expression in peripheral blood was analyzed by FACS (FIG. 13). CD11b was used as a marker of myeloid cells. With the CMV promoter 3% of the peripheral leukocytes were CD11b+/GFP+ and 15% were CD11b−/GFP+, whereas with SP #144 5% of cells were CD11b+/GFP+ and only 0.5% were CD11b−/GFP+, demonstrating the specificity in vivo of the super-myeloid promoters (FIG. 13). Also, SP-GFP lentivector-transduced mouse myeloid cells showed higher GFP expression than CMV-GFP lentivector-transduced mouse cells (compare middle and right panels of FIG. 13). However, fewer than two thirds of the myeloid cells (CD11b+) were GFP+, suggesting low transduction efficiency in this experiment. The average proviral copy number measured by real-time PCR was 0.7 in the genomic DNA isolated from peripheral blood of the recipient (data not shown). In an experiment using higher titer ($1.0\times10^9$ IU/ml) CMV-GFP lentivector in the transduction, a higher proviral copy number (~3.1) was obtained and 85% of the leukocytes were GFP+, although the mean fluorescence intensity was low (FIG. 14), as reported by other investigators. These data are consistent with a recent report on gene therapy of murine β-thalassemia (Imren et al., *Proc Natl Acad Sci USA,* 99:14380-85, 2002), which demonstrated that pan-erythroid correction required high titer (~$1.5\times10^9$) lentivector. A lower titer ($2\times10^8$) viral preparation resulted in a lesser proportion of erythrocytes expressing human β-globin due to incomplete transduction of donor HSCs and position effect variegation of cells with a single integrated copy.

Figure 15:
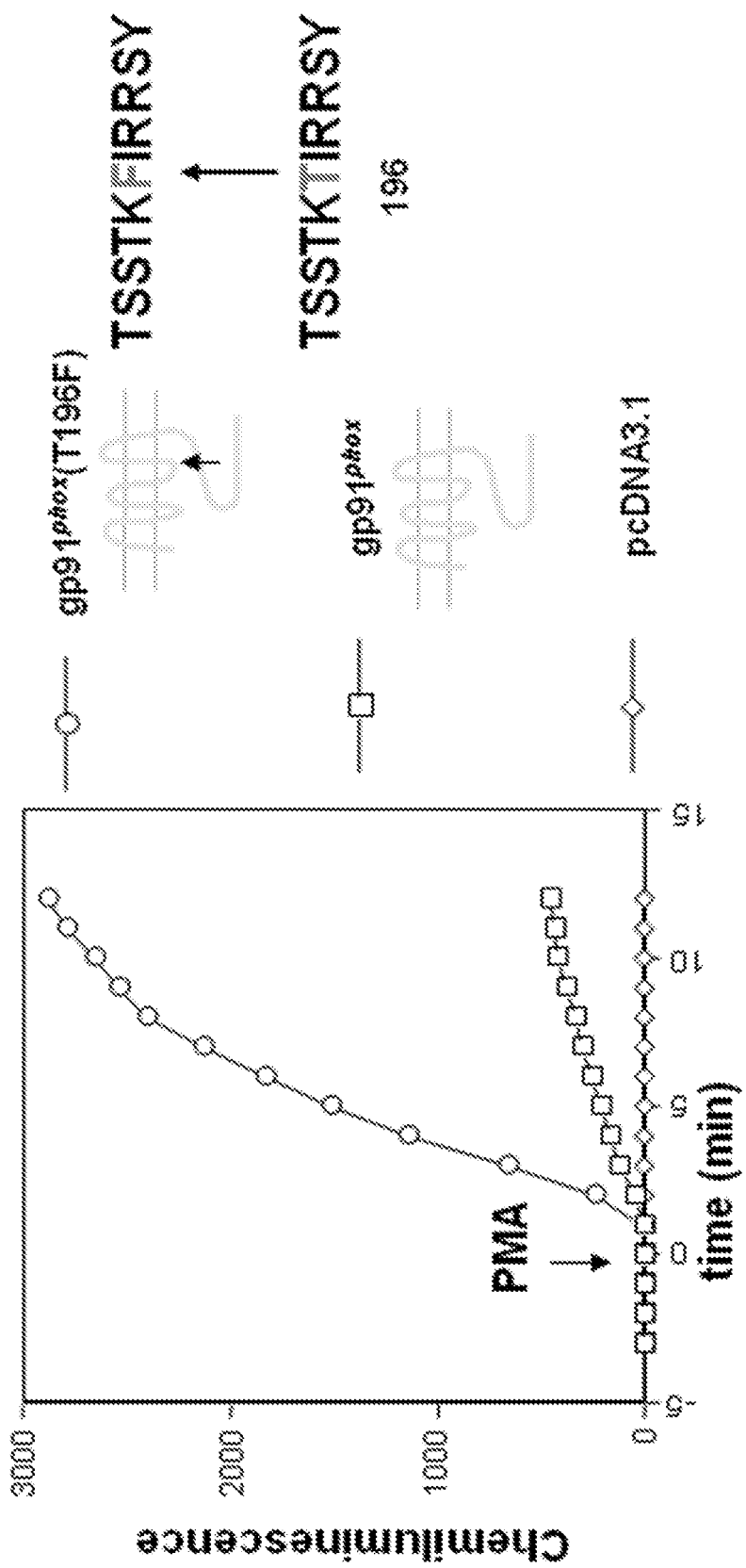
FIG. 15. The gp91$^{phox}$ (T196F) mutant is superactive compared with wild-type. A cellular luminescence enhancement system for superoxide detection (Diogenes, National Diagnostics) was used. Human p47$^{phox}$ and p67$^{phox}$ stably expressing K562 cells were transfected with either wild-type human gp91$^{phox}$ vector, gp91$^{phox}$ (T196F) vector, or empty vector pcDNA 3.1 48 h before measurement. K562 cells constitutively express p22$^{phox}$ and Rac. The experiment shown is representative of 3 studies.

Super-Active Gp91$^{phox}$ Mutant:

In a structure/function study of gp91$^{phox}$, a super-active variant of gp91$^{phox}$ (T196F) was generated in which residue 196 is mutated from threonine to phenylalanine (FIG. 15). PMA-stimulated superoxide generation was 7-fold greater when gp91$^{phox}$(T196F), versus wild-type gp91$^{phox}$, was used to reconstitute the NADPH oxidase in K562 cells. The mutant construct was made by Quik-Change™ site-directed mutagenesis of gp91$^{phox}$ using sense primer CCTCCAC-CAAATTCATCCGGAGGTC (SEQ ID NO:1) and anti-sense primer GACCTCCGGATGAATTTGGTGGAGG (SEQ ID NO:2). The construct was sequenced and subcloned into fresh pcDNA3.1 (−) using NheI and XhoI.

Figure 16:
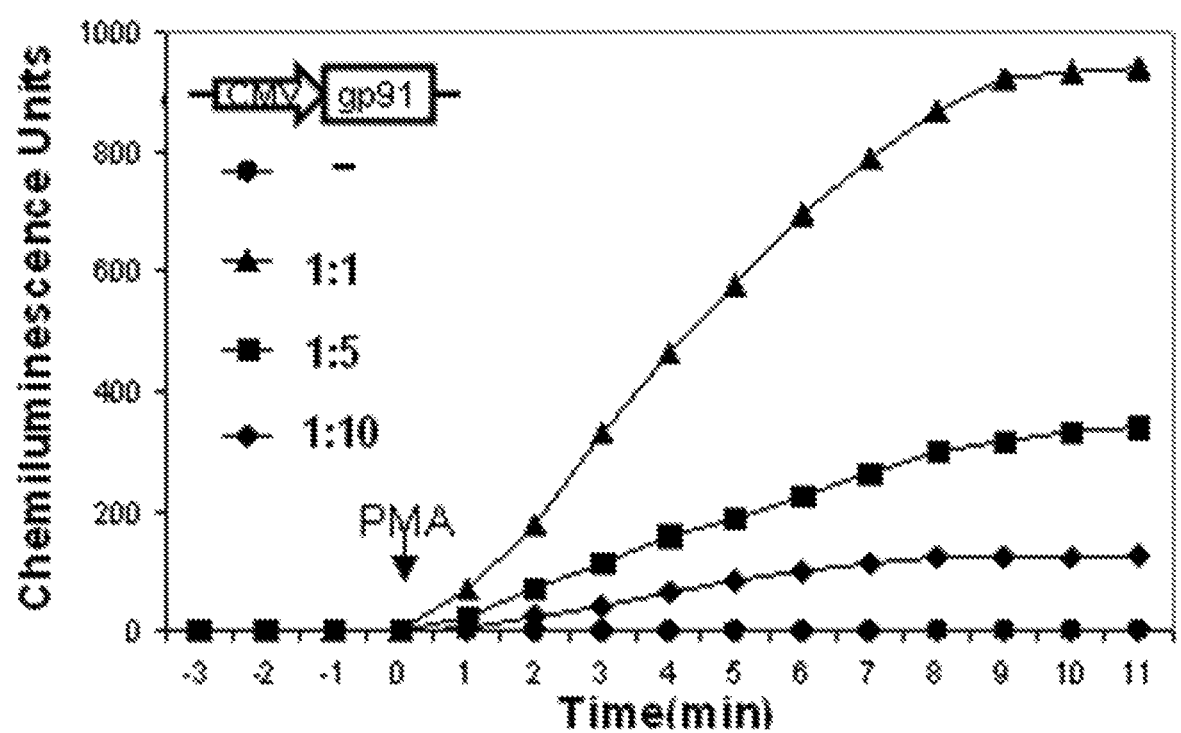
FIG. 16. gp91$^{phox}$ expression by lentiviral vectors. Superoxide assay was done 48 h post-transduction by CMV-gp91$^{phox}$ lentivirus with different dilutions as indicated. The concentrations of lentivirus used in transduction correlated well with the amounts of superoxide generated in A2 cells, indicating the success of the cloning procedure, lentiviral production and transduction of cells.

Gp91$^{phox}$ Expressing Lentivector Production and Transduction:

To gain experience in lentiviral expression of human gp91$^{phox}$, the cDNA was inserted into a replication-incompetent third-generation lentivector (gift of Dr. Didier Trono, University of Geneva, Switzerland) downstream of the CMV promoter. The insert and its flanking regions were fully sequenced to confirm the identity. This lentivector is self-inactivating, stripped of all HIV accessory proteins, and strictly dependent on complementation of Rev protein in trans. VSV-G-pseudotyped lentivector CMV-EGFP particles were generated by transient co-transfection of the specific transfer vector plasmid with the 3 packaging plasmids (pMDLg/pRRE, the gag-pol plasmid; pRSV-Rev, a Rev expressing plasmid; and pMD-G, a VSV-G envelope expressing plasmid) into 293T cells by calcium phosphate or Fugen6 transfection reagents. Two days after transfection, the culture medium with various dilutions was used to transduce the A2 cell line (K562 cells bearing stably expressing human p47$^{phox}$ and p67$^{phox}$ vectors). Sixty hours later, the cells were processed for superoxide measurement using the Diogenes reagent. As shown in FIG. 16, lentivector-gp91$^{phox}$ transduction could reconstitute NADPH oxidase activity in the cells in a dose-dependent manner.

Figure 17:
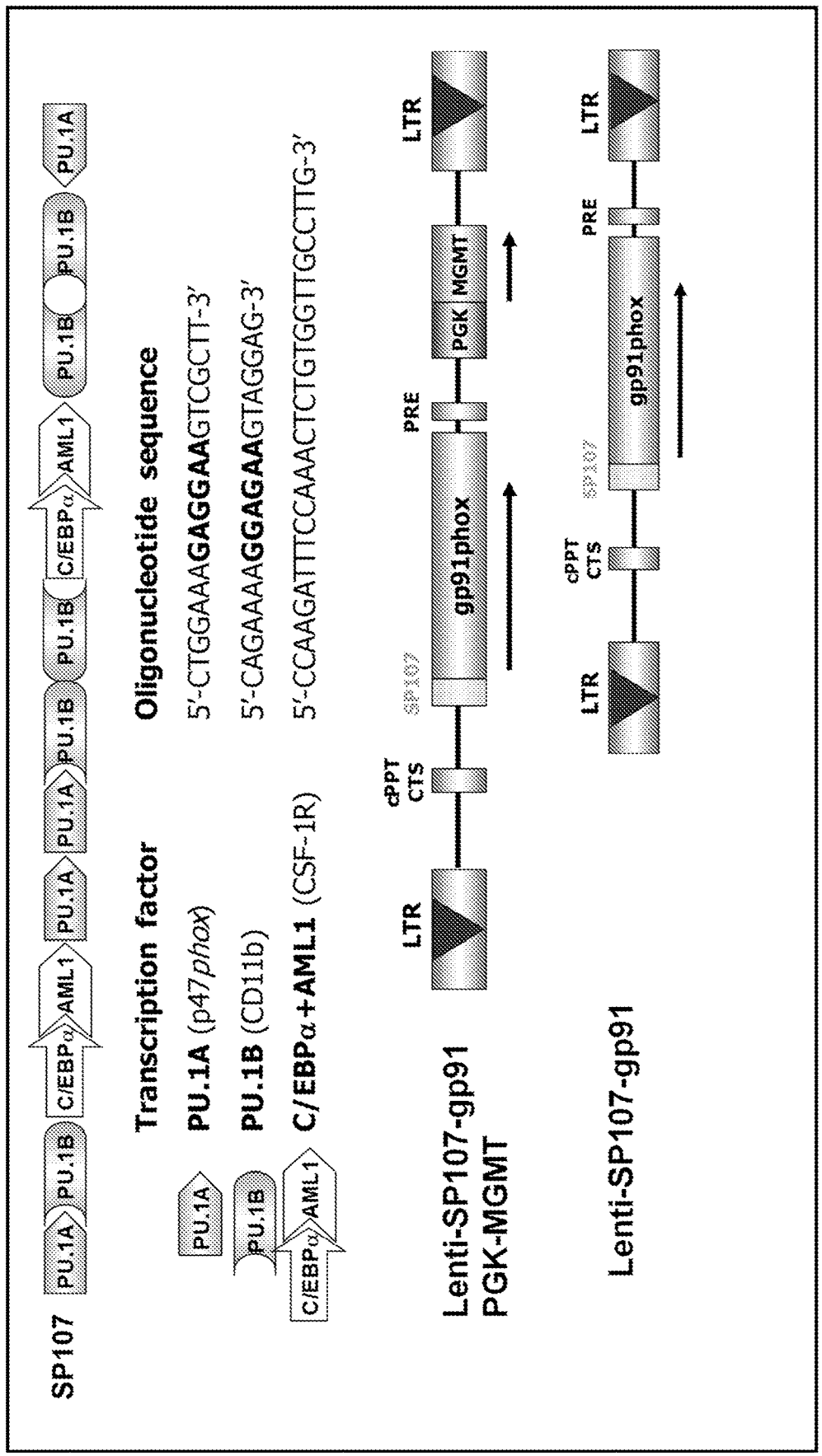
FIG. 17. Vector construction (SEQ ID NO: 38-40).

X-CGD Gene Therapy with Lentiviral Vectors in a Mouse Model:

Two myeloid-specific lentiviral expression vectors were constructed and designated as Lenti-SP107-gp91-PGK-MGMT and Lenti-SP107-gp91 (FIG. 17). Lenti-SP107-gp91 viruses were produced and used to transduce murine X-CGD bone marrow cells. Transduced cells were transplanted into lethally irradiated syngeneic X-CGD mice. After hematologic recovery, superoxide production, as monitored by DHR flow cytometric analysis, was detected in 20 to 50% of peripheral blood neutrophils at 27 weeks after transplantation (FIG. 18) (Bjorgvinsdottir et al., *Blood*, 89:41-48, 1997).

Validation of the Super-Myeloid Promoters in Transgenic Mice Using EGFP (Enhanced Green Fluorescent Protein) as a Reporter:

Transgenic mice are made with the super-promoter-EGFP cassette flanked by a 1.2 kb DNA fragment of chromatin insulator to avoid silencing of the transgene. Transgene copy number is assessed by Southern blot analysis. To check expression of the transgene, peripheral blood leukocytes, peritoneal cells, bone morrow cells, and splenocytes are isolated and analyzed by FACS for co-expression of EGFP with leukocyte markers. EGFP transcripts and protein in various tissues are tested by Northern and Western blot analyses, respectively. Promoters with the greatest strength and tissue-specificity for neutrophils and macrophages are used in subsequent studies.

Correct $Gp91^{phox}$-Deficiency in Mice by Syngeneic Transplantation of HSC Transduced Ex Vivo with Lentivector Expressing the $Gp91^{phox}$ Gene Driven by the Super-Promoters (SP):

Human $gp91^{phox}$ and its variant $gp91^{phox}$ (T196F) cDNA are separately inserted into Lenti-SP-GFP to replace the EGFP gene. The resulting constructs, Lenti-SP-$hgp91^{phox}$, Lenti-SP-$hgp91^{phox}$ (T196F), and the parent vector Lenti-SP-GFP are co-transfected respectively by Fugene6 reagents together with the 3 packaging plasmids into 293T cells to produce lentiviral particles, which are then concentrated by ultra-centrifugation and used to transduce mouse X-CGD bone marrow stem cells ex vivo for 5-6 hours. The transduced bone marrow cells are infused into lethally irradiated X-CGD recipient mice by tail vein injection. For each construct, 20 mice are used as recipients and analyzed for the proportion of superoxide-generating cells in peripheral neutrophils by nitroblue tetrazolium (NBT) testing or dihydrorhodamine 123 (DHR) flow cytometric analysis. Whole cell superoxide production is quantified using a luminol-based chemiluminescence reagent (Diogenes), and by a spectrophotometric assay of cytochrome C reduction. Expression of the transgenes is determined in various lineages of bone marrow cells by RT-PCR and Western blot analysis. Provirus copy number in the genome of blood cells are measured using real-time PCR. Reconstitution of host defense is examined by *A. fumigatus* and *B. cepacia* challenges. Secondary X-CGD transplantation is carried out to confirm integration of the functional provirus in reconstituting stem cells.

Correct $p47^{phox}$-Deficiency in Mice by Syngeneic Transplantation of HSC Transduced Ex Vivo with Lentivector Expressing the $Gp47^{phox}$ Gene Driven by SMP:

Both murine and human $p47^{phox}$ cDNA are used. The assessment of reconstitution of NADPH oxidase function and host defense is as described herein. Many viral promoters, such as CMV, show strong promoter activity, but are generally active in a wide variety of cell types. Lacking cell specificity, they may drive inappropriate gene expression in non-target tissues and cells causing additional problems to the recipient. Moreover, viral promoters are vulnerable to gene silencing (Persons and Nienhuis, *Proc Natl Acad Sci USA*, 97:5022-24, 2000; Malik et al., *Blood*, 86:2993-3005, 1995) which is a major problem encountered both in transgenic mice and in gene therapy. Furthermore, earlier studies found that the level of expression of $gp91^{phox}$ protein resulting from transfection with a CMV-driven lentivector was probably inadequate for clinical application. More recently, the human EF1α promoter in SIN lentivectors has been reported to achieve a significant improvement in transgene expression when HSCs were the target (Brenner and Malech, *Biochim Biophys Acta*, 1640:1-24, 2003; Galimi and Verma, *Curr Top Microbiol Immunol*, 261:245-54, 2002; Roesler et al., *Blood*, 100:4381-90, 2002). In gene therapy generally, there is a pressing need for strong tissue or cell-specific promoters; in the context of this disclosure, strong myeloid specific promoters.

Certain synthetic promoters are almost two-fold more active in myeloid (CD11b positive) cells compared with a CMV promoter, but inactive in other blood cell lineages in a bone marrow recipient mouse. Recent findings that bone marrow stem cells (probably mesenchymal stem cells) can trans-differentiate into various non-hematopoietic cell types such as neurons and endothelial cells (Jiang et al., *Nature*, 418:41-49, 2002; Hubner et al., *Science*, 300:1251-56, 2003; Horwitz et al., *Proc Natl Acad Sci USA*, 99:8932-37, 2002) support full characterization of these super-promoters in vivo. From a total of about a dozen super synthetic promoters, the five with the highest activity and specificity in vitro are tested for their strength and tissue specificity in transgenic mice. EGFP is used as a reporter gene. The EGFP gene encodes a protein with a single red-shifted excitation peak and 30- to 40-fold more fluorescence intensity than wild-type GFP when excited at 488 nm (Shariatmadari et al., *Biotechniques*, 30:1282-85, 2001).

Transgenic mice are made with the super promoter-EGFP cassette, flanked by a 1.2 kb DNA fragment of chromatin insulator to avoid silencing of the transgene (Recillas-Targa et al., *PNAS USA*, 96:14354-59, 1999). The promoter showing the greatest strength and tissue-specificity for myeloid expression in vivo is used in gene therapy studies.

In consideration of moving into clinical trials, both human $gp91^{phox}$ and human $p47^{phox}$ in addition to murine $p47^{phox}$ gene is used in the study on CGD gene therapy. Human $gp91^{phox}$ and $p47^{phox}$ have been shown to work well in CGD mouse models (Dinauer et al., *Blood*, 94:914-22, 1999; Bjorgvinsdottir et al., *Blood*, 89:41-48, 1997; Mardiney et al., *Blood*, 89:2268-75, 1997). The murine and human $gp91^{phox}$ and $p47^{phox}$ protein sequences are highly similar, and exhibit cross-species complementation of respiratory burst oxidase activity in human and murine CGD phagocytes cultured in vitro (Bjorgvinsdottir et al., *Blood*, 89:41-48, 1997).

Characterization of the Synthetic Super Myeloid Promoters in Transgenic Mice Using EGFP as a Reporter.

Construction of Synthetic Promoter-EGFP Reporter Transgene.

Figure 18:
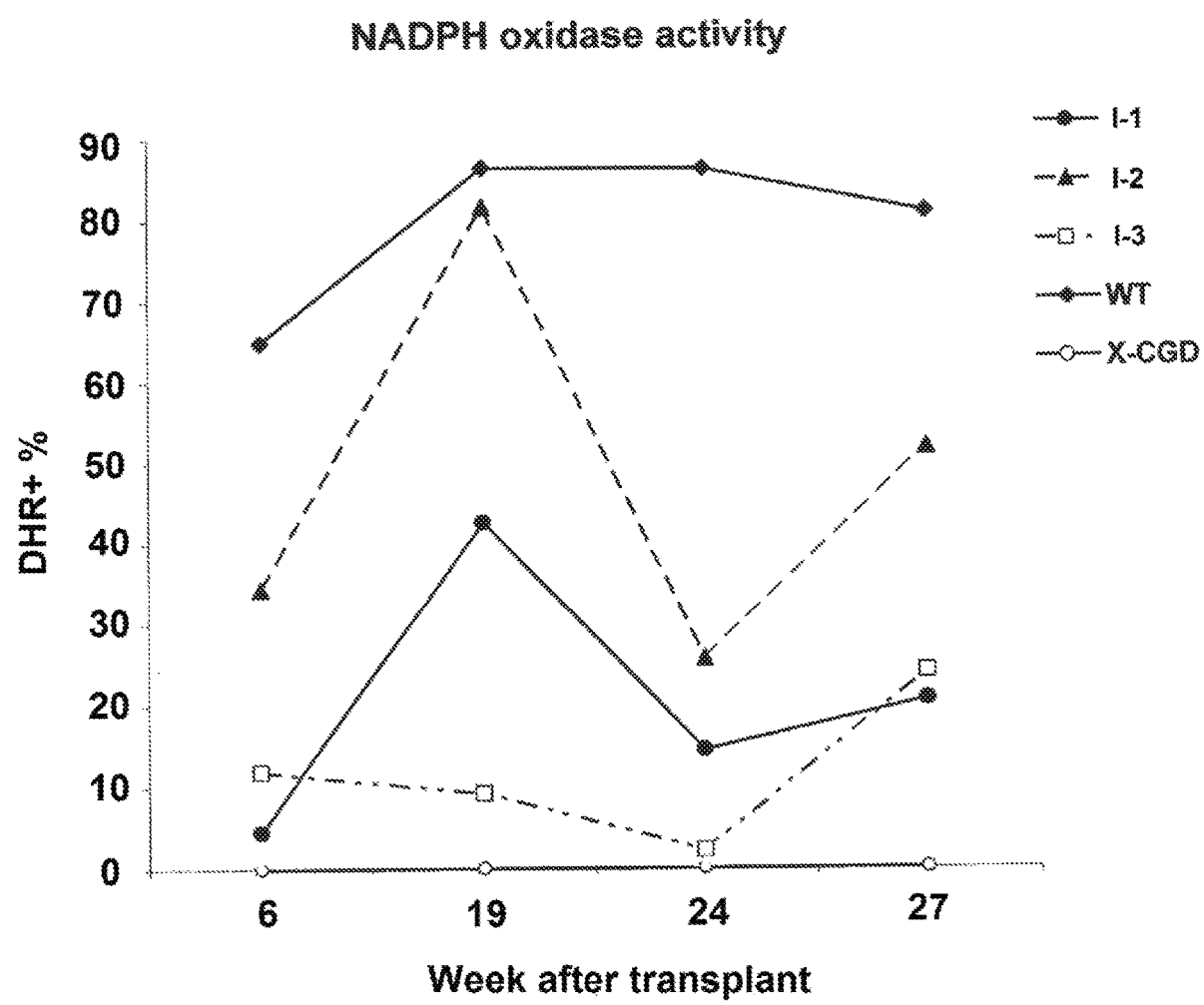
FIG. 18. Lenti-SP107-gp91 (Monocistronic) in X-CGD mice.

The pEGFPC1-SP constructs are modified so that the transcriptional unit will be flanked by a 1.2 kb DNA fragment of chromatin insulator (a kind gift from Dr. Gary Felsenfeld, NIH, Bethesda) to avoid gene silencing (FIG. 18). In the construction process, restriction enzyme sites are included to facilitate release of the transgene DNA fragment that contains the least vector sequences. Initially, three powerful clones pEGFPC1-SP-107, pEGFPC1-SP-144, and pEGFPC1-SP-146 are modified for making transgenic mice. Plasmid DNA is prepared either by Qiagen EndoFree Plasmid kit or by twice CsCl-Ethidium bromide gradient to ensure DNA quality.

Generation of SP-EGFP Transgenic Mice.

The DNA is injected into C57BL6/J zygotes at a concentration 3 ng/μl. Transgenic founder mice are identified by PCR and the results confirmed by Southern blotting. Founder mice are mated with C57BL/6 mice, and progeny screened 3-4 weeks of age for the presence of the transgene by PCR using genomic DNA isolated from tail biopsy samples. They are bred to homozygosity before experiments to reduce the work load in the later identification of transgene bearing mice, and to eliminate variation of gene expression introduced by genomic volume.

Assessment of Transgene Copy Number by Southern Blotting.

The copy number of a transgene has been shown to contribute to the subsequent levels of gene expression (Rhoades et al., Blood, 96:2108-15, 2000; Fedorov et al., Genesis, 31:78-84, 2001). Although it is hard to predict, higher copy number often leads to higher expression levels. Therefore, the copy number of the transgene is determined by comparison with defined amounts of the DNA used for pronuclear injections.

Southern Blot Analysis.

Genomic DNA is isolated by proteinase K digestion and phenol/chloroform extraction, digested with restriction enzymes, subjected to 0.7-1.2% agarose gel electrophoresis, and then transferred to a nylon membrane (NEN Life Science Products, Boston Mass.). Membranes are prehybridized for 30 min at 65° C. in hybridization buffer (50 mM Tris, pH 7.4, 1 M NaCl, 1% SDS, and 10% PEG 8000). Hybridization is carried out overnight with a specific $^{32}$P-labeled probe at 65° C. Blots are washed for 20 min at 65° C. four times with 0.1×SSC, 0.5% SDS. The membranes are exposed to X-ray film at −70° C.

Isolation of Leukocytes, Peritoneal Cells, Bone Marrow, and Splenocytes.

Peripheral blood leukocytes are isolated by separation in Ficoll-Hypaque gradients, hypotonic lysis in 0.15 mmol/L $NH_4Cl$, 1 mmol/L $KHCO_3$, 0.1 mmol/L EDTA followed by washing in PBS. Peritoneal cells are isolated by peritoneal lavage with 20 ml PBS at times indicated after the intraperitoneal administration of 1 ml of a 10% solution of thioglycollate (DIFCO, Detroit, Mich.). Bone marrow is flushed from femurs and tibias with PBS (Dziennis et al., Blood, 85:319-29, 1995; Hahn et al., PNAS USA, 95:14880-85, 1998). Splenocytes are isolated using 70 μm cell strainers (FALCON). Spleen tissue will be rubbed into 5 ml tissue cell wash buffer (DMEM medium containing 2% FCS, 1% P/S, 10 mM HEPES). To collect the single-cell suspension, the tube is placed in ice for 5 min, the supernatant transferred to a fresh tube, and 1 ml of red blood cell lysis buffer (Sigma) is added for 1-3 min to lyse the red blood cells. The remaining spleen cells are adjusted to $2 \times 10^6$/ml for immunoflorescence staining (Back et al., Blood, 85:1017-24, 1995).

Immunoflorescence Staining and FACS Analysis for the Co-Expression of EGFP with Leukocyte Markers.

To detect macrophage/monocytes, neutrophils and T cells, CD11b or CD68, Gr-1, and CD4 are used as cell surface markers respectively, using either direct or indirect immunoflorescence staining. For CD11b on macrophage/monocytes, Gr-1 on neutrophils and CD4 on T cells, direct immunoflorescence staining is used. $10^6$ cells are washed in cold PBS containing 0.5% BSA (0.5% BSA/PBS), and incubated with either specific conjugated anti-mouse antibody or the corresponding conjugated $IgG_{2\alpha}$ (control) for 15 min at 4° C. in 100 μl 0.5% BSA/PBS. After washing, cells are subjected to FACS analysis immediately or by using 1% formalin to fix cells, the analysis is done the next day. The antibodies used include APC-conjugated anti-mouse CD11b, PerCP-conjugated anti-mouse CD4 and PE-conjugated anti-MOUSE Gr-1. As controls, the corresponding conjugated immunoglobulin isotype is used. FITC conjugated antibody are not used because of interference with the green florescence of GFP. To detect CD68 on macrophage/monocytes, indirect immunoflorescence is used. $10^6$ cells are stained by a BAC immunostaining system, using goat anti-mouse CD68 (polyclonal IgG), biotin-conjugated rabbit anti-goat Ig and APC-conjugated streptavidin in that order. Cells are washed after each step in PBS (Blum, Nat Neurosci, 1:374-77, 1998; Ho and Blum, J Neurosci, 18:5614-29, 1998).

Detection of EGFP in Frozen Sections by Fluorescence and Confocal Microscopy Using a Slow Freezing Protocol.

Animals are anesthetized with Rompun, xylazine and Ketaset (1:1) and killed by intracardiac perfusion with 1% paraformaldehyde in 0.15 M phosphate buffer, pH 7.2 (PBS), followed by 4% paraformaldehyde. Tissues are dissected, washed once in PBS, and embedded in Tissue-Tek at room temperature. The embedded tissues are kept in the dark at 4° C. for 34 h and then slowly frozen at −70° C. in a box covered with cotton wool. The tissues can be stored at −70° C. for one, two, and six weeks before sectioning. The fluorescent light emitted by EGFP is evaluated using by confocal microscopy (Olympus FluoView™ 500). The tissue sections are exposed to a 488 nm excitation wavelength and emission obtained at 500-520 nm. Ten images with 2 μm intervals in the z-axis are collected (Shariatmadari et al., Biotechniques, 30:1282-85, 2001).

Double Immunolabeling.

To better identify EGFP-expressing cells, double immunolabeling is used. Tissue sections are processed for combined fluorescence immunocytochemistry for EGFP (rabbit polyclonal anti-EGFP1:250; Clontech, Palo Alto, Calif.) and CD68 (goat polyclonal IgG, 1:50; Santa Cruz, Calif.), EGFP and Gr-1 (PE anti-mouse Gr-1, 1:100; Pharmingen, San Diego, Calif.), EGFP and CD4 (PerCP anti-mouse CD4; 1:100; Pharmingen, San Diego, Calif.) (Blum, Nat Neurosci, 1:374-77, 1998).

Northern Blot Analysis.

RNA is size-fractionated on 1.0% agarose gels containing 2.2 M formaldehyde and transferred to nylon membranes (Gene Screen Plus; NEN DuPont) by using a transblot apparatus (Bio-Rad) in 10×SSC (1×SSC is 0.15 M NaCl and 0.015 M citrate). Blots are hybridized overnight to radiolabeled probes in the presence of 1% SDS, 10% dextran sulfate, 1 mM NaCl, and 50% formamide at 42° C. After hybridization, membranes are washed twice with 2×SSC for 5 min each at room temperature, twice with 2×SSC containing 1% SDS or 0.1% SDS at 60° C. for 30 min, and twice with 0.05×SSC at room temperature for 15 min prior to autoradiography.

Western Blot Analysis.

Western blotting is used to monitor EGFP expression in various tissues. Animals are sacrificed and their hearts, livers, spleens, lungs, kidneys, and brains dissected and lysed in extraction buffer (40 mM Tris, pH 6.8, 2% 2-mercaptoethanol, 1% SDS, 5% glycerol, 10 mM EDTA, 50 μg/ml aprotinin, 50 μg/ml leupeptin, 500 μg/ml Pefabloc and 10 μg/ml pepstatin A). Samples are boiled for 5 min and insoluble debris removed by centrifugation for 3 min at 12,000 g. The protein concentration of the cleared supernatant is determined using the DC Protein Assay kit (BioRad Labs., Hercules, Calif.). Extracted cellular proteins (80 μg/sample) are fractionated by SDS-PAGE and electrophoretically transferred to nitrocellulose (BA85; 0.45 μm, Midwest Scientific, Valley Park, Mo.). Blots are pretreated in PBS blocking buffer (5% NFDM, 0.2% Tween-20 in PBS) for 1 h at 23° C. and then incubated in blocking buffer for 2 h at 23° C. with a polyclonal anti-EGFP (Clontech).

Antigen-antibody complexes are visualized by enhanced chemiluminescence (SuperSignal kit, Pierce, Inc., Rockford, Ill.).

Example 2

Correction of gp91$^{phox}$ Deficiency by Bone Marrow Transplantation Combined with Ex Vivo Lentiviral Transduction of a Super-Promoter (Sp)-gp91$^{phox}$ Gene Mice.

C57Bl/6J wild-type and X-CGD (gp91$^{phox}$−/) mice are obtained from either the inventors colony or from Jackson Laboratories (Bar Harbor, Me.). Mice with a null allele for gp91$^{phox}$ were generated initially by targeted disruption of the gp91$^{phox}$ locus in 129-SV murine embryonic stem cells by Dr. Dinauer and backcrossed for more than 11 generations with wild-type C57Bl/6J mice (Dinauer et al., *Blood*, 94:914-22, 1999). Genotyping of mice is performed using polymerase chain reaction of tail blood and confirmed by nitroblue tetrazolium (NBT) testing of peripheral blood (PB) neutrophils (Clark, *J Infect Dis*, 161: 1140-1147, 1990). Mice are maintained under specific pathogen-free conditions and fed autoclaved food and acidified water. BMT mice receive drinking water with 100 mg/liter neomycin and 10 mg/liter polymyxin B for 3 days before and 14 days after transplantation.

Lentiviral Vector Construction.

The replication incompetent 3rd generation lentivectors are gifts from Dr. Didier Trono (Geneva, Switzerland) (Miyoshi et al., *J Virol*, 72:8150-57, 1998). They are self-inactivating, stripped of all HIV accessory proteins, and strictly dependent on complementation of Rev protein in trans. The CMV-EGFP or EF-1α-EGFP cassette is replaced with SP-hgp91$^{phox}$ and SP-hgp91$^{phox}$ (T196F).

Lentiviral Vector Production.

VSV-G-pseudotyped lentivector-SP-hgp91$^{phox}$ or -SP-hgp91$^{phox}$ (T196F) particles are generated by transient cotransfection of the specific transfer vector plasmid with the 3 packaging plasmids (pMDLg/pRRE, the gag-pol plasmid; pRSV-Rev, a Rev expressing plasmid; and pMD.G, a VSV-G envelope expressing plasmid) into 293T cells. Lentivector supernatant is filtered, concentrated by twice ultracentrifugation (55,000 g for 3 hours), and stored at 70° C. (Pawliuk et al., *Science*, 294:2368-71, 2001; Imren et al., *PNAS USA*, 99:14380-85, 2002). The viral titers are estimated by transduction of 293T cells with the CMV-EGFP lentivector processed simultaneously.

Bone Marrow Cell Culture, Lentiviral Infection and Transplantation.

Isolation, transduction, and transplantation of murine X-CGD BM cells is essentially as previously described (Imren et al., PNAS USA, 99:14380-85, 2002). Briefly, bone marrow (BM) is obtained from femurs and tibias of 6- to 8-week-old X-CGD male mice 4 days after i.v. injection of 5-FU at a dose of 100 mg/kg body weight. Bone marrow cells are treated with Lympholyte-M (Gibco, Cat #10639-011) for enrichment of HSCs, and stimulated overnight in StemPro medium along with 6 ng/ml of IL-3, 10 ng/ml of IL-6, 10 ng/ml of murine IL-1α and 100 ng/ml of Stem Cell factor. The next day, cells are pelleted and resuspended in 0.85 ml of the aforementioned medium containing the same growth factor combination with concentrated, vesicular stomatitis virus glycoprotein-G-pseudotyped SP-gp91$^{phox}$ lentivectors at a final virus concentration of 2-10×10$^9$ infectious units/ml. Infection are performed for 5 h on fibronectin-coated Petri dishes in the presence of 8 μg/ml protamine sulfate. After infection, 2×10$^6$ cells are transplanted, without selection, by i.v. injection into each syngeneic recipient given 950 cGy of total body irradiation.

Secondary Bone Marrow Transplantation (BMT) of X-CGD Mice.

Secondary BMT is performed to confirm that integration of functional lentivector-gp91$^{phox}$ provirus has occurred in reconstituting stem cells. BM from primary recipients is harvested 8 to 11 months post-transplantation and used for secondary transplants (Bjorgvinsdottir et al., Blood, 89:41-48, 1997).

Gp91$^{phox}$ Expression in Peripheral Blood Neutrophils and Monocytes/Macrophages. Gene-corrected gp91$^{phox}$-null, untreated control gp91$^{phox}$-null, and wild-type mice are bled by tail venisection. Two hundred microliters of whole blood is placed in polypropylene tubes and lysed with prewarmed ammonium chloride lysis buffer (pH 8.0). Cells are washed once and then resuspended in 400 μL of Hanks' Buffered Saline Solution (HBSS, without Ca$^{2+}$, Mg$^{2+}$, or phenol red), 0.5 g albumin (human fraction V), and 1 ml of 0.5 mol/L EDTA (pH 8.0). Cells are analyzed by flow cytometry to determine coexpression of murine CD3 (all leukocytes) and CD11b (myeloid cells), or Gr-1 (granulocytes) with human gp91$^{phox}$ detected using fluorescein isothiocyanate (FITC)-conjugated murine monoclonal antibody 7D5, which does not bind to mouse gp91$^{phox}$ (Dinauer et al., *Blood*, 94:914-22, 1999; Bjorgvinsdottir et al., *Blood*, 89:41-48, 1997).

Phagocyte NADPH Oxidase Activity.

Nitroblue tetrazolium (NBT) dye (Sigma, St Louis, Mo.) reduction to formazan precipitate is used as a measure of superoxide production at the cellular level. The NBT assay is performed on tail blood PB neutrophils allowed to adhere to a glass slide for 15 to 20 minutes or on BM-derived neutrophils allowed to adhere to a chamber slide (Nunc, Inc, Naperville, Ill.) for 1 hour before activation of the respiratory burst oxidase with phorbol myristate acetate (PMA) (Dinauer et al., *Blood*, 94:914-22, 1999). After incubation for 20 to 30 minutes at 37° C., slides are fixed and counterstained with safranin and the percentage of NBT-positive cells (containing blue-purple formazan deposits from reduction of NBT) determined by evaluating 100 to 200 cells using light microscopy. A similar protocol is used to examine phagocyte oxidase activity in peritoneal exudate macrophages.

NADPH oxidase activity is also tested by flow cytometric analysis of PB neutrophils using the dihydrorhodamine 123 (DHR) assay as described (Vowells et al., *J Immunol Methods*, 178:89-97, 1995). Briefly, gene-corrected gp91$^{phox}$-null, untreated control gp91$^{phox}$-null, and wild-type mice are bled by tail venisection. Two hundred microliters of whole blood is placed in polypropylene tubes and lysed with prewarmed ammonium chloride lysis buffer (pH 8.0). Cells are washed once and then resuspended in 400 μl of Hanks' Buffered Saline Solution (HBSS, without Ca2+, Mg2+, or phenol red), 0.5 g albumin (human fraction V), and 1 ml of 0.5 mol/L EDTA (pH 8.0). 1.8 μl of 29 mmol/L DHR, and 5 μL of catalase (1,400 U/μL) is added to each tube, which are then incubated for 5 min in a 37° C. shaking water bath. After 5 min, 100 μl of 3.2×10$^3$ nmol/L PMA is added to each reaction tube and the tubes are returned to the water bath for an additional 14 min. After incubation, all samples are immediately analyzed by flow cytometry using a FACSort (Becton Dickinson Immunocytometry System [BDIS], San Jose, Calif.) with CellQuest software (BDIS). Neutrophils are identified based on forward and side scatter characteristics. However, with mouse blood it is not possible to establish a gate including most neutrophils that completely excludes lymphocytes. For this reason, the data for experimental p47$^{phox}$−/−mice is adjusted to reflect the results with wild-type mice. Each sample is run in the setup mode until a neutrophil acquisition gate is established, at which point only events in this gate are acquired. At least 10,000 events are collected in this gate in all studies. Analysis of neutrophil DHR fluorescence is performed by constructing a side scatter/FL2 dot plot and DHR-positive cells identified by gating based on negative (untreated p47$^{phox}$−/−) and positive wild-type control samples. The experimental mice are bled and evaluated 1 week before transplantation (baseline analysis), 1 month after transplantation, and every 2 weeks thereafter.

NADPH oxidase activity is measured in a population of neutrophils using a luminol-based chemiluminescence assay (Diogenes) of superoxide production. Isolated neutrophils are resuspended in Krebs-Ringer-Glucose buffer (KRG), and kept on ice while viable counts are determined. $5 \times 10^5$ cells are transferred to luminometer tubes, pelleted, and resuspended in 75 μl KRG. 100 μl of Diogenes reagent (National Diagnostics) is added, and the baseline chemiluminescence at 37° C. is monitored for 0.5 seconds every minute for 3 minutes. Samples are kept at 37° C. between readings. 25 μl of 16 μg/ml PMA are then added to stimulate superoxide production, and readings are taken every minute for 40 minutes in a Luminoskan luminometer (Promega). This is sufficient time in each case to reach a peak rate of photon emission. Total photon emission over this period is taken as the measurement of superoxide output.

A continuous assay of superoxide-dismutase-inhibitable ferricytochrome c reduction is used to quantitate absolute levels of superoxide formation (e.g. nmol/min/10$^6$ cells) by PMA-stimulated BM-derived neutrophils, as described previously (Clark et al. *J Biol Chem*, 262:4065-74, 1987). The cell compartment of the dual-beam spectrophotometer is kept at 37° C. with a circulating water system. Cuvettes of 0.5-ml capacity quartz cells and with black masked sides are used (Spectrocell, Inc., Oreland, Pa.). The sample cuvette will contain 0.1 mM ferricytochrome C in PiCM buffer (138 mM NaCl, 2.7 mM KCl, 0.6 mM CaCl$_2$), 1.0 mM MgCl$_2$, 10 mM phosphate buffer, pH 7.4), isolated cells, electron donor (NADPH), and activating agent (PMA) in a total volume of 0.5 ml. The reference cuvette contains the same reagents plus 62.5 μg/ml of superoxide dismutase. After initiation of the reaction with PMA, the net increase in absorbance at 550 nm (sample minus reference) is followed for several minutes. The rate of superoxide production is calculated based on a specific extinction coefficient for ferrocytochrome C of 21.1/mM/cm (Pawliuk et al., *Science*, 294: 2368-2371, 2001).

Isolation of Neutrophil-Enriched BM Cells and Peritoneal Exudate Macrophages. BM cells are flushed from hind limbs and neutrophil-enriched fractions obtained essentially as described previously (Dinauer et al., *Blood*, 94:914-22, 1999) by either isolating the non-adherent cell population (approximately 50% to 60% mature neutrophils as determined by examination of Wright's-stained cytospin preparations) or by discontinuous Percoll density gradient centrifugation (70% to 90% mature neutrophils). Neutrophil-enriched preparations are maintained on ice in 1× Hanks' balanced salt solution (HBSS) without Ca2+ or Mg2+ with 1% glucose and 0.1% BSA until further processing for NADPH oxidase assay and/or extraction of protein, RNA, or DNA.

For isolation of peritoneal exudate macrophages, mice are injected with aged thioglycollate broth by intraperitoneal injection, and 72 hours later, exudate cells (approximately 90% macrophages) are isolated by peritoneal lavage as previously described (Dinauer et al., *Blood*, 94:914-22, 1999). Cells are incubated on ice as described above for neutrophil-enrichment before assay for NADPH oxidase activity and for RNA extraction.

Isolation of T and B Cells.

To demonstrate the myeloid specificity of the promoters further, lymphocytes are analyzed for lack of expression. Spleens are disaggregated to obtain a single cell suspension, and low-density mononuclear cells isolated by centrifugation on Ficoll 1119. Cells are labeled with biotin-conjugated anti-mouse CD3 or CD45R/B220 monoclonal antibodies (PharMingen, San Diego, Calif.) for purification of T- and B-cell fractions respectively, using the MiniMACS (Miltenyi Biotec, Auburn, Calif.) magnetic cell separation system according to the manufacturer's instructions. Extracts for protein, RNA, and/or DNA are then prepared as described below. Analysis of immunoselected cells by staining and flow cytometry shows greater than 98% purity. In some cases, total thymus is extracted for protein and/or nucleic acids analysis (Dinauer et al., *Blood*, 94:914-22, 1999; Bjorgvinsdottir et al., *Blood*, 89:41-48, 1997).

PB Counts.

To examine whether the hematopoiesis is altered by the proposed manipulation, PB counts (hematocrit, white blood cell, differential, and reticulocyte counts) are determined at various times post-transplant using blood obtained from the tail vein. In some cases, blood is obtained either from the retro-orbital plexus or from the inferior vena cava postmortem for platelet counts (Bjorgvinsdottir et al., *Blood*, 89:41-48, 1997).

DNA, RNA, and Immunoblot Analysis.

These will be done using similar procedures as described above.

Real-Time PCR Analysis of Proviral Copy Number.

Vector copy number in mouse peripheral blood cells is determined by real-time quantitative TaqMan polymerase chain reaction (PCR) (PE Applied Biosystems, Foster City, Calif.). Primers and probes completely within the extended LTR lentivector sequence are used that can be used regardless of the transgene (gp91$^{phox}$ or p47$^{phox}$). Forward primer, TGAAAGCGAAAGGGAAACCA (SEQ ID NO:3); 6FAM-labeled probe, AGCTCTCTCGACGCAGGACTC (SEQ ID NO:4); reverse primer, CCGTGCGCGCTTCAG (SEQ ID NO:5). In some cases, gp91$^{phox}$ cDNA will be targeted: forward primer, GTCGAAATCTGCTGTCCTTCCT (SEQ ID NO:6); 6FAM-labeled probe, TTCCAGTGCGTGCTGCTCAACAAGA (SEQ ID NO:7); reverse primer, TTCGAAGACAACTGGACAGGAAT (SEQ ID NO:8). The following incubation periods are applied for all primer sets: 2 min at 50° C., 10 min at 95° C., 40 cycles of 15 sec at 95° C., and 60 sec at 60° C. Standard curves for the TaqMan PCR analyses are obtained by using vector single-copy clones of NIH 3T3 cells transduced with the lentiviral vector (Roesler et al., *Blood*, 100:4381-90, 2002).

*Aspergillus fumigatus* Infection.

X-CGD mice have a marked impairment in host defense to the opportunistic fungus, *A. fumigatus*. Although wild-type mice are resistant to respiratory challenge with millions of *A. fumigatus* conidia, as few as 50 conidia always resulted in chronic and sometimes fatal bronchopneumonia in X-CGD mice. Mice are infected by intratracheal instillation of *A. fumigatus* conidia (spores) obtained from a clinical isolate (ATCC No. 90240; American Tissue Culture Center, Rockville, Md.), as previously described (Dinauer et al.,

*Blood,* 97:3738-45, 2001). The test doses are 150 or 500 conidia per animal. The number of conidia in the inoculum are confirmed by plate culture. The trachea is exposed in mice anesthetized with ketamine, acepromazine, and atropine and the inoculum is instilled through a 24G angiocath (Becton Dickinson Vascular Access, Sandy, Utah) in 35 μL of sterile saline containing 5% colloidal carbon (Eberhard Faber, Inc, Lewisburg, Tenn.) to allow localization of the inoculum to each lung. As prophylaxis against secondary bacterial infection, mice are given intramuscular injection of Ceftriaxone (Rocephin; Hoffman-La Roche, Nutley, N.J.) 1.25 mg per animal immediately before infection, and again 24 hours later, followed by oral Tetracycline (Polyotic; American Cyanamid Co, Wayne, N.J.) 5 mg/ml in the drinking water for the remainder of the experiment. Mice are examined daily, and electively killed by cervical dislocation 17 to 21 days after challenge with *A. fumigatus*. Lungs are removed and inflated and fixed in neutral buffered formalin for histologic examination of paraffin-embedded sections obtained from carbon-stained regions of lung. Sections are stained with hematoxylin and eosin for assessment of pathological changes or Grocott methamine silver for assessment of hyphae. Findings used to score for *A. fumigatus* lung disease, based on previous studies in murine X-CGD (Galimi and Verma, *Curr Top Microbiol Immunol,* 261:245-54, 2002; Bjorgvinsdottir et al., *Blood,* 89:41-48, 1997) include areas of purulent bronchopneumonia, granulomas with mixed inflammatory cell infiltrate, and presence of hyphae or abscesses.

Burkholderia cepacia Infection.

*B. cepacia* is an opportunistic gram-negative pathogen that can produce serious infections in patients with CGD, including pneumonia and associated sepsis. In a recent report on a national registry of 368 CGD patients, *B. cepacia* sepsis/pneumonia was the second most lethal infection on patients. Mice are injected intraperitoneally with a 0.5 ml saline suspension containing various numbers of *B. cepacia* bacilli (clinical isolate from bronchial washings; ATCC No. 25609; ATCC) at 12 to 14 weeks posttransplantation. Animals are monitored daily and killed if moribund. Tail venisection is performed to determine bacteremia for 7 to 8 days after challenge with $10^6$ colony-forming unit (CFU) or greater per mouse and for 15 to 17 days after challenge with $10^5$ CFU or less per mouse. Bacteremia is quantitated by plate culture. Blood is diluted in sterile water at 1:10 to lyse blood cells; further 10-fold serial dilutions of the lysed blood are plated in semi-soft agar (Becton Dickinson, Cockeysville, Md.) and colonies enumerated 48 hours after incubation at 37° C. (Dinauer et al., *Blood,* 97:3738-45, 2001).

Staphylococcus aureus Infection.

*S. aureus* is a common cause of soft tissue or visceral abscesses in CGD patients. Dr. Dinauer has previously found that clearance of *S. aureus* from the peritoneal cavity is impaired in X-CGD mice compared with wild-type mice after intraperitoneal injection of a sublethal dose of *S. aureus*. Mice are injected intraperitoneally with 0.2 ml suspension of $1 \times 10^8$/ml *S. aureus* strain 502A (ATCC No. 27217; ATCC), as previously described (Dinauer et al., *Blood,* 97:3738-45, 2001). The number of bacteria in the inoculum are confirmed by plate culture of serial dilutions. Mice are examined daily and killed 7 days after peritoneal challenge. The presence of Staphylococcal intraperitoneal abscesses are assessed by visual inspection, and the organism is confirmed by culture and Gram stain.

Safety Testing.

Because the gp91$^{phox}$-deficient mice have a protein-null phenotype of X-CGD and human gp91$^{phox}$ is expressed as transgene, mouse serum is tested for the development of antibody specific to human gp91$^{phox}$ by SDS/PAGE and immunoblot detection. Genomic DNA from peripheral blood cells is screened for the presence of replication competent retrovirus by using a PCR assay to detect sequence encoding the envelope (Brenner and Malech, *Biochim Biophys Acta,* 1640:1-24, 2003; Galimi and Verma, *Curr Top Microbiol Immunol,* 261:245-54, 2002; Roesler et al., *Blood,* 100:4381-90, 2002).

Example 3

Correction of p47$^{phox}$-Deficiency by Bone Marrow Transplantation Combined with Ex Vivo Lentiviral Transduction of Sp-p47$^{phox}$ Gene Animals.

p47$^{phox}$-/- mice are provided by Dr. Steven Holland at NIH. Gene deletions were created in the 129 background strain and bred on C57BL/6 as described. Heterozygous deletants were crossed back onto the C57BL/6 background and then intercrossed (Jackson et al., *J Exp Med,* 182:751-58, 1995). p47$^{phox}$-/- mice and wild-type littermates are used for the described experiments. Genotyping of mice is performed using polymerase chain reaction of tail blood and confirmed by NBT testing of peripheral blood neutrophils. Mice are maintained under specific pathogen-free conditions and fed autoclaved food and acidified water. In addition, all p47$^{phox}$-/- mice are maintained on Bactrim prophylaxis (30 mg/kg), except during and after bacterial challenge studies.

Other Procedures.

Lentivector construction, viral production, transduction of HSC, bone marrow transplantation, assessment of NADPH oxidase reconstitution and host defense will be done in the same fashion as described herein.

Statistical Analysis.

ANOVA is used to examine any statistical difference among groups, followed by Newman-Keuls comparison or Bonferroni comparison analysis. For the infection challenge studies, statistical analysis using the Fischer exact test or the Mann-Whitney nonparametric test with 2-tailed P values are performed by using Instat 2.0 software. Log rank-tests for equality of survival is performed using GB-Stat version 6.5 software (Dynamic Microsystems, Silver Spring, Md.) (Dinauer et al., *Blood,* 97:3738-45, 2001).

The invention claimed is:

1. A method of administering therapeutic hematopoietic stem cells (HSC) engineered to express gp91$^{phox}$ to a subject in need of treatment for chronic granulomatous disease comprising:
   (a) mobilizing stem cells in the bone marrow of the subject by administering granulocyte-colony stimulating factor (G-CSF) to the subject to form an empty stem cell niches in the bone marrow without exposing the subject to chemotherapy or irradiation conditioning;
   (b) administering the therapeutic HSCs engineered to express gp91$^{phox}$, derived from autologous HSCs, intravenously, wherein the therapeutic HSCs engineered to express gp91$^{phox}$ localize in the empty bone marrow stem cell niche formed in step (a); and
   (c) repeating steps (a) and (b) four or more times.

2. The method of claim 1, wherein the therapeutic HSCs are produced from autologous HSCs prior to administration ex vivo by lentiviral transduction of a super-promoter (SP)-gp91$^{phox}$ gene.

3. The method of claim 1, further comprising administering a second mobilization agent concurrently the granulocyte-colony stimulating factor (G-CSF) stem cell mobilization agent.

4. The method of claim 3, wherein the second mobilization agent is AMD3100.

* * * * *

SEQUENCE LISTING

```
<160> NUMBER OF SEQ ID NOS: 40

<210> SEQ ID NO 1
<211> LENGTH: 25
<212> TYPE: DNA
<213> ORGANISM: Artificial Sequence
<220> FEATURE:
```

<223> OTHER INFORMATION: Synthetic Primer

<400> SEQUENCE: 1
cctccaccaa attcatccgg aggtc                                       25

<210> SEQ ID NO 2
<211> LENGTH: 25
<212> TYPE: DNA
<213> ORGANISM: Artificial Sequence
<220> FEATURE:
<223> OTHER INFORMATION: Synthetic Primer

<400> SEQUENCE: 2
gacctccgga tgaatttggt ggagg                                       25

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
tgaaagcgaa agggaaacca                                             20

<210> SEQ ID NO 4
<211> LENGTH: 21
<212> TYPE: DNA
<213> ORGANISM: Artificial Sequence
<220> FEATURE:
<223> OTHER INFORMATION: Synthetic Primer

<400> SEQUENCE: 4
agctctctcg acgcaggact c                                           21

<210> SEQ ID NO 5
<211> LENGTH: 15
<212> TYPE: DNA
<213> ORGANISM: Artificial Sequence
<220> FEATURE:
<223> OTHER INFORMATION: Synthetic Primer

<400> SEQUENCE: 5
ccgtgcgcgc ttcag                                                  15

<210> SEQ ID NO 6
<211> LENGTH: 22
<212> TYPE: DNA
<213> ORGANISM: Artificial Sequence
<220> FEATURE:
<223> OTHER INFORMATION: Synthetic Primer

<400> SEQUENCE: 6
gtcgaaatct gctgtccttc ct                                          22

<210> SEQ ID NO 7
<211> LENGTH: 25
<212> TYPE: DNA
<213> ORGANISM: Artificial Sequence
<220> FEATURE:
<223> OTHER INFORMATION: Synthetic Primer

<400> SEQUENCE: 7
ttccagtgcg tgctgctcaa caaga                                       25

```
<210> SEQ ID NO 8
<211> LENGTH: 23
<212> TYPE: DNA
<213> ORGANISM: Artificial Sequence
<220> FEATURE:
<223> OTHER INFORMATION: Synthetic Primer

<400> SEQUENCE: 8
ttcgaagaca actggacagg aat                                             23

<210> SEQ ID NO 9
<211> LENGTH: 16
<212> TYPE: DNA
<213> ORGANISM: Artificial Sequence
<220> FEATURE:
<223> OTHER INFORMATION: Synthetic Primer

<400> SEQUENCE: 9
aaagaggaag tcgctt                                                     16

<210> SEQ ID NO 10
<211> LENGTH: 72
<212> TYPE: DNA
<213> ORGANISM: Artificial Sequence
<220> FEATURE:
<223> OTHER INFORMATION: Synthetic Primer

<400> SEQUENCE: 10
gggctcgagg taccctccct gcccctgtc ccgaccgcga caaaagcgac ttcctctttc      60
cagtgcattt aa                                                         72

<210> SEQ ID NO 11
<211> LENGTH: 73
<212> TYPE: PRT
<213> ORGANISM: Artificial Sequence
<220> FEATURE:
<223> OTHER INFORMATION: Synthetic Primer

<400> SEQUENCE: 11

Thr Thr Ala Ala Ala Thr Gly Cys Ala Cys Thr Gly Gly Ala Ala Ala
1               5                   10                  15

Gly Ala Gly Gly Ala Ala Gly Thr Cys Gly Cys Thr Thr Thr Thr Gly
            20                  25                  30

Thr Cys Gly Cys Gly Gly Thr Cys Thr Gly Gly Ala Cys Ala Gly Gly
        35                  40                  45

Gly Gly Gly Gly Cys Ala Gly Gly Ala Gly Gly Gly Thr Ala Cys Cys
    50                  55                  60

Thr Cys Gly Ala Gly Cys Cys Cys
65                  70

<210> SEQ ID NO 12
<211> LENGTH: 34
<212> TYPE: DNA
<213> ORGANISM: Artificial Sequence
<220> FEATURE:
<223> OTHER INFORMATION: Synthetic Primer

<400> SEQUENCE: 12
gggctcgagg acttcctctt tccagtgcat ttaa                                 34

<210> SEQ ID NO 13
<211> LENGTH: 34
<212> TYPE: DNA
<213> ORGANISM: Artificial Sequence
```

```
<220> FEATURE:
<223> OTHER INFORMATION: Synthetic Primer

<400> SEQUENCE: 13
ttaaatgcac tggaaagagg aagtcctcga gccc                                   34

<210> SEQ ID NO 14
<211> LENGTH: 32
<212> TYPE: DNA
<213> ORGANISM: Artificial Sequence
<220> FEATURE:
<223> OTHER INFORMATION: Synthetic Primer

<400> SEQUENCE: 14
gggctcgagc ttcctctttc cagtgcattt aa                                     32

<210> SEQ ID NO 15
<211> LENGTH: 32
<212> TYPE: DNA
<213> ORGANISM: Artificial Sequence
<220> FEATURE:
<223> OTHER INFORMATION: Synthetic Primer

<400> SEQUENCE: 15
ttaaatgcac tggaaagagg aagctcgagc cc                                     32

<210> SEQ ID NO 16
<211> LENGTH: 22
<212> TYPE: DNA
<213> ORGANISM: Artificial Sequence
<220> FEATURE:
<223> OTHER INFORMATION: Synthetic Primer

<400> SEQUENCE: 16
gggctcgagc cagtgcattt aa                                                22

<210> SEQ ID NO 17
<211> LENGTH: 22
<212> TYPE: DNA
<213> ORGANISM: Artificial Sequence
<220> FEATURE:
<223> OTHER INFORMATION: Synthetic Primer

<400> SEQUENCE: 17
ttaaatgcac tggctcgagc cc                                                22

<210> SEQ ID NO 18
<211> LENGTH: 26
<212> TYPE: DNA
<213> ORGANISM: Artificial Sequence
<220> FEATURE:
<223> OTHER INFORMATION: Synthetic Primer

<400> SEQUENCE: 18
gccactcatt gaggaagtga aagatg                                            26

<210> SEQ ID NO 19
<211> LENGTH: 26
<212> TYPE: DNA
<213> ORGANISM: Artificial Sequence
<220> FEATURE:
<223> OTHER INFORMATION: Synthetic Primer

<400> SEQUENCE: 19
agcctagaaa gaggaactag cacgag                                            26
```

<210> SEQ ID NO 20
<211> LENGTH: 25
<212> TYPE: DNA
<213> ORGANISM: Artificial Sequence
<220> FEATURE:
<223> OTHER INFORMATION: Synthetic Primer

<400> SEQUENCE: 20
ctcagaatag gggagggca ggaca                                          25

<210> SEQ ID NO 21
<211> LENGTH: 32
<212> TYPE: DNA
<213> ORGANISM: Artificial Sequence
<220> FEATURE:
<223> OTHER INFORMATION: Synthetic Primer

<400> SEQUENCE: 21
tcagccttca ggctgttttt ggcttgaagg tg                                 32

<210> SEQ ID NO 22
<211> LENGTH: 26
<212> TYPE: DNA
<213> ORGANISM: Artificial Sequence
<220> FEATURE:
<223> OTHER INFORMATION: Synthetic Primer

<400> SEQUENCE: 22
gctgatgtac ttcctctctc ctccac                                        26

<210> SEQ ID NO 23
<211> LENGTH: 26
<212> TYPE: DNA
<213> ORGANISM: Artificial Sequence
<220> FEATURE:
<223> OTHER INFORMATION: Synthetic Primer

<400> SEQUENCE: 23
ggtagggtta tgagtcagtt gccaaa                                        26

<210> SEQ ID NO 24
<211> LENGTH: 27
<212> TYPE: DNA
<213> ORGANISM: Artificial Sequence
<220> FEATURE:
<223> OTHER INFORMATION: Synthetic Primer

<400> SEQUENCE: 24
gtggggacat ttcctgatgc attttgc                                       27

<210> SEQ ID NO 25
<211> LENGTH: 11
<212> TYPE: DNA
<213> ORGANISM: Artificial Sequence
<220> FEATURE:
<223> OTHER INFORMATION: Synthetic Primer

<400> SEQUENCE: 25
acctaatcat g                                                        11

<210> SEQ ID NO 26
<211> LENGTH: 265
<212> TYPE: DNA
<213> ORGANISM: Artificial Sequence
<220> FEATURE:
<223> OTHER INFORMATION: Synthetic Primer

<400> SEQUENCE: 26

| | | | | |
|---|---|---|---|---|
| gtccacttcc tcaatttctg tgcagctggg aggtgaggta agaggaagtg tgggccacag | | | | 60 |
| gctaggccca gagagcctgg aggaggagcc tctgccagac tggagagaag caggcctgag | | | | 120 |
| cctccccaaa ggcagctcct ggggactccc aggaccacag gctgagacga gacgcagggt | | | | 180 |
| ggctggagga agtgagaggt gaactcagcc tgggactggc tgggcgagac tctccacctg | | | | 240 |
| ctccctggga ccatcgccca ccatg | | | | 265 |

<210> SEQ ID NO 27
<211> LENGTH: 26
<212> TYPE: DNA
<213> ORGANISM: Artificial Sequence
<220> FEATURE:
<223> OTHER INFORMATION: Synthetic Primer

<400> SEQUENCE: 27
gagggtccac ttcctcaatt tctgtg                                    26

<210> SEQ ID NO 28
<211> LENGTH: 26
<212> TYPE: DNA
<213> ORGANISM: Artificial Sequence
<220> FEATURE:
<223> OTHER INFORMATION: Synthetic Primer

<400> SEQUENCE: 28
gagggtccac ttggtcaatt tctgtg                                    26

<210> SEQ ID NO 29
<211> LENGTH: 26
<212> TYPE: DNA
<213> ORGANISM: Artificial Sequence
<220> FEATURE:
<223> OTHER INFORMATION: Synthetic Primer

<400> SEQUENCE: 29
ggtgaggtaa gaggaagtgt gggcca                                    26

<210> SEQ ID NO 30
<211> LENGTH: 26
<212> TYPE: DNA
<213> ORGANISM: Artificial Sequence
<220> FEATURE:
<223> OTHER INFORMATION: Synthetic Primer

<400> SEQUENCE: 30
ggtgaggtaa gaccaagtgt gggcca                                    26

<210> SEQ ID NO 31
<211> LENGTH: 26
<212> TYPE: DNA
<213> ORGANISM: Artificial Sequence
<220> FEATURE:
<223> OTHER INFORMATION: Synthetic Primer

<400> SEQUENCE: 31
agggtggctg gaggaagtga gaggtg                                    26

<210> SEQ ID NO 32
<211> LENGTH: 26
<212> TYPE: DNA
<213> ORGANISM: Artificial Sequence
<220> FEATURE:

```
<223> OTHER INFORMATION: Synthetic Primer

<400> SEQUENCE: 32
agggtggctg gaccaagtga gaggtg                                    26

<210> SEQ ID NO 33
<211> LENGTH: 20
<212> TYPE: DNA
<213> ORGANISM: Artificial Sequence
<220> FEATURE:
<223> OTHER INFORMATION: Synthetic Primer

<400> SEQUENCE: 33
ctggaaagag gaagtcgctt                                           20

<210> SEQ ID NO 34
<211> LENGTH: 20
<212> TYPE: DNA
<213> ORGANISM: Artificial Sequence
<220> FEATURE:
<223> OTHER INFORMATION: Synthetic Primer

<400> SEQUENCE: 34
cagaaaagga gaagtaggag                                           20

<210> SEQ ID NO 35
<211> LENGTH: 30
<212> TYPE: DNA
<213> ORGANISM: Artificial Sequence
<220> FEATURE:
<223> OTHER INFORMATION: Synthetic Primer

<400> SEQUENCE: 35
ccaagatttc caaactctgt ggttgccttg                                30

<210> SEQ ID NO 36
<211> LENGTH: 20
<212> TYPE: DNA
<213> ORGANISM: Artificial Sequence
<220> FEATURE:
<223> OTHER INFORMATION: Synthetic Primer

<400> SEQUENCE: 36
gggttatgag tcagttgcca                                           20

<210> SEQ ID NO 37
<211> LENGTH: 21
<212> TYPE: DNA
<213> ORGANISM: Artificial Sequence
<220> FEATURE:
<223> OTHER INFORMATION: Synthetic Primer

<400> SEQUENCE: 37
ctgagcctcc gccctcttcc t                                         21

<210> SEQ ID NO 38
<211> LENGTH: 20
<212> TYPE: DNA
<213> ORGANISM: Artificial Sequence
<220> FEATURE:
<223> OTHER INFORMATION: Synthetic Primer

<400> SEQUENCE: 38
ctggaaagag gaagtcgctt                                           20
```

```
<210> SEQ ID NO 39
<211> LENGTH: 20
<212> TYPE: DNA
<213> ORGANISM: Artificial Sequence
<220> FEATURE:
<223> OTHER INFORMATION: Synthetic Primer

<400> SEQUENCE: 39
cagaaaagga gaagtaggag                                              20

<210> SEQ ID NO 40
<211> LENGTH: 30
<212> TYPE: DNA
<213> ORGANISM: Artificial Sequence
<220> FEATURE:
<223> OTHER INFORMATION: Synthetic Primer

<400> SEQUENCE: 40
ccaagatttc caaactctgt ggttgccttg                                   30
```